(12) United States Patent
Dib et al.

(10) Patent No.: US 12,364,505 B2
(45) Date of Patent: *Jul. 22, 2025

(54) HANDLE ASSEMBLY FOR MEDICAL DEVICES

(71) Applicant: Dib UltraNav Medical LLC, El Paso, TX (US)

(72) Inventors: Nabil Dib, El Paso, TX (US); Brad Knight, Brooklyn Park, MN (US); Charmaine Dwyer, El Paso, TX (US); Michael Nagel, El Paso, TX (US); Lowry Barfield, El Paso, TX (US)

(73) Assignee: Dib UltraNav Medical LLC, El Paso, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/501,701

(22) Filed: Nov. 3, 2023

(65) Prior Publication Data

US 2024/0074785 A1 Mar. 7, 2024

Related U.S. Application Data

(63) Continuation of application No. 17/139,836, filed on Dec. 31, 2020, now Pat. No. 11,864,791.

(60) Provisional application No. 63/002,851, filed on Mar. 31, 2020.

(51) Int. Cl.
*A61B 17/34* (2006.01)
*A61B 17/00* (2006.01)
*A61B 50/20* (2016.01)

(52) U.S. Cl.
CPC .... *A61B 17/3415* (2013.01); *A61B 17/00234* (2013.01); *A61B 50/20* (2016.02); *A61B 2017/00243* (2013.01); *A61B 2017/3407* (2013.01); *A61B 2017/3413* (2013.01); *A61B 2017/3486* (2013.01)

(58) Field of Classification Search
CPC .......... A61B 17/3415; A61B 17/00234; A61B 50/20
USPC ............................................................ 606/1
See application file for complete search history.

(56) References Cited

U.S. PATENT DOCUMENTS

| | | | |
|---|---|---|---|
| 5,599,299 A | 2/1997 | Weaver et al. |
| 6,129,734 A | 10/2000 | Shturman et al. |
| 6,702,748 B1 | 3/2004 | Nita et al. |
| 6,731,963 B2 | 5/2004 | Finarov et al. |
| 11,864,791 B2 | 1/2024 | Dib et al. |
| 2007/0293724 A1 | 12/2007 | Saadat et al. |

(Continued)

FOREIGN PATENT DOCUMENTS

| | | |
|---|---|---|
| WO | 2011/011269 A2 | 1/2011 |
| WO | 2016/041792 A1 | 3/2016 |

OTHER PUBLICATIONS

International Search Report and Written Opinion mailed May 24, 2021 for International Application Serial No. PCT/US2020/067724 filed on Dec. 31, 2020.

(Continued)

*Primary Examiner* — Nadia A Mahmood
(74) *Attorney, Agent, or Firm* — K&L Gates LLP; Louis C. Cullman; Hal Gibson

(57) ABSTRACT

A handle apparatus comprising void regions or attachment devices that accommodate the shape of surgical devices and imaging units such that the device is held securely and mechanically fixed to the imaging unit within the handle assembly.

20 Claims, 18 Drawing Sheets

(56) References Cited

U.S. PATENT DOCUMENTS

| | | | |
|---|---|---|---|
| 2008/0269862 A1* | 10/2008 | Elmouelhi | A61B 18/1492 |
| | | | 74/519 |
| 2010/0041990 A1 | 2/2010 | Schlitt et al. | |
| 2011/0208062 A1 | 8/2011 | Baraso et al. | |
| 2012/0172838 A1 | 7/2012 | Flaherty et al. | |
| 2013/0053694 A1 | 2/2013 | Roschak et al. | |
| 2013/0226218 A1 | 8/2013 | Binmoeller | |
| 2014/0188146 A1 | 7/2014 | Nita et al. | |
| 2015/0230690 A1 | 8/2015 | Frankel et al. | |
| 2017/0027607 A1 | 2/2017 | Verbeek et al. | |
| 2017/0172541 A1 | 6/2017 | Yamashita | |
| 2019/0083063 A1 | 3/2019 | Okubo et al. | |

OTHER PUBLICATIONS

Extended European Search Report issued Feb. 20, 2024 for European Patent Application No. 20928170.8.

* cited by examiner

HANDLE ASSEMBLY FOR MEDICAL DEVICES

CROSS-REFERENCE TO RELATED APPLICATIONS

The application is a continuation of U.S. patent application Ser. No. 17/139,836, filed Dec. 31, 2020, which claims priority to U.S. Provisional Patent Application No. 63/002,851 filed Mar. 31, 2020, the entire contents of each of which are incorporated by reference herein in their entirety.

FIELD

The present Specification relates to systems, methods, and devices for controlling medical device placement, coordination, and operation.

BACKGROUND

Use of what would be considered a "medical device" by modern standards dates as far back as 7000 BC, when Neolithic dentists used flint-tipped drills and bowstrings. Medical devices vary in both their intended use and indications for use. Examples range from simple, low-risk devices such as tongue depressors, thermometers, disposable gloves, and bedpans, to complex implanted devices. Medical devices help health care providers diagnose and treat sickness or disease, improving patient quality of life.

In medicine, a catheter is a thin tube made from medical grade materials serving a broad range of functions. Catheters can be inserted in the body to treat diseases or perform surgical procedures. Cardiac catheterization is a procedure used to diagnose and treat certain cardiovascular conditions. During cardiac catheterization, the long thin tube is inserted into an artery or vein in the groin, neck, or arm, and threaded through blood vessels to the heart.

Currently, cardiac catheterization procedures, performed for example on the cardiac structure, such as septal puncture, catheter ablation, valve repair or replacement, diagnostics, and left appendage closure, utilize separate, mechanically distinct, imaging (such as ultrasound) and procedural equipment (such as a needle or ablation tool), which can lead to loss or impairment of visualization, for example during heart motion. As a result, current methods are time consuming, costly, and involve poor visualization procedures that can result in undesirable events such as perforation of the septum. These shortcomings have been attributed at least in part to poor imaging of the catheter and secondary instruments, often due to shortcomings in coordinating the use of the surgical and imaging units.

SUMMARY

Disclosed herein are methods, systems, and devices for coordinating, controlling, and operating medical equipment, for example equipment such as surgical devices such as hand-held surgical devices including, for example, catheters, imaging systems, needles, ablation equipment, and the like, and combinations thereof.

Disclosed herein are integrated multi-device systems and uses thereof. Disclosed systems are compatible with, for example, multiple catheters, imaging devices, and other surgical devices.

Disclosed embodiments can comprise a "handle assembly" comprising a lumen, and a shell, housing, or frame, that increases the degree of control and precision of surgical instrument use by mechanically "fixing" the position of multiple instruments relative to each other.

In embodiments, the handle assembly provides attachment points such as locks, clips, void regions, snaps, and combinations thereof to reversibly attach, for example, multiple devices such as a surgical devices including procedural devices such as needles and imaging devices such as ultrasound units, to the shell, housing, or frame, as well as providing a comfortable, secure grip for the operator. In embodiments the handle assembly encloses (at least partially) the surgical devices. In embodiments the handle assembly provides an attachment frame for the surgical devices to attach-to. Disclosed handle assemblies can comprise "complimentary" void regions shaped to accommodate the shape of, for example, multiple surgical devices such as catheters, imaging, and procedural devices.

Disclosed embodiments can comprise at least one lumen for insertion into a patient, for example to accommodate the handle assembly-attached surgical devices or lumens used with the devices. In embodiments, the at least one lumen can comprise multiple interior lumens along at least a portion of the device. For example, in embodiments, the disclosed handle assemblies can comprise more than one lumen opening toward the distal end of the device, and fewer lumens at the proximal end of the device, wherein the more than one lumens join together to form the fewer lumens.

Disclosed systems and devices can "fix" or maintain the position of multiple instruments in relation to each other, for example fix the position of a procedural surgical device, for example a catheter comprising a needle, in relation to a localization device, for example a catheter comprising an imaging unit, that allows the operator to better-visualize the precise location of the surgical device, or a portion of the device, for example the operative portion of the device such as the tip of a needle or surgical tool, so as to more precisely control cardiac procedures, such as catheter/septum perforation locations, measurement of chamber dimensions of the heart, procedures on valves or other heart structures, and combinations thereof.

Disclosed systems and methods provide the ability to localize, for example to image, a catheter tip, a secondary instrument, and the target tissue in a single image, with the catheter positioned in a forward-looking position relative to a target tissue, for example a heart valve, which can reduce procedure time and increase success rate. Embodiments eliminate the need for a reflective catheter tip.

In contrast to systems and devices of the prior art, disclosed handle assemblies and systems can incorporate multiple surgical devices into a single entity, for example integrating both imaging units such as ultrasound, and surgical devices such as a procedural catheter, into a single system. These integrated systems enable simpler procedures, lower cost, reduce staffing requirements, and are safer and more effective because of the accuracy of visualization.

Disclosed methods comprise catheterization, for example cardiac catheterization, which includes a number of procedures wherein access to the heart is obtained through a peripheral artery or vein. Commonly, this includes the radial artery, internal jugular vein, and femoral artery/vein. Once access is obtained, catheters are used to navigate to and around the heart. Catheters come in numerous shapes, lengths, diameters, number of lumens, and other special features such as needles, cutting tools, electrodes and balloons. Once in place, they can be used to measure or medically intervene. Imaging is an important aspect to catheterization and commonly includes fluoroscopy, but can also include forms of echocardiography (TTE, TEE, ICE) and ultrasound (IVUS).

Disclosed embodiments comprise methods for cardiac catheterization, for measuring pressure in the four chambers of the heart, taking samples of blood to measure oxygen content in the four chambers of the heart, identifying and measuring atrial and ventricular septum, atrial appendage, pulmonary veins, defects in the valves or chambers of the heart, biopsy, and the like.

Disclosed embodiments can comprise diagnosis and/or treatment of, for example:
a. Septal puncture;
b. Cardiomyopathy: Enlargement of the heart due to thickening or weakening of the heart muscle;
c. Congenital heart disease: Defects in one or more heart structures formed during fetal development;
d. Heart failure: A condition in which the heart muscles become too weak to pump blood well, leading to congestion in the blood vessels and lungs;
e. Heart valve disease: Failure of one or more heart valves, leading to reduced blood flow within the heart;
f. Arrhythmias such as atrial fibrillation ablations;
g. Left atrial appendage closure;
h. Peri-valvular leak;
i. PFO (patent Foramen ovalis) and ASD (atrial Septal Defect) closure;
j. Percutaneous Ventricular assist devices;
k. Hemodynamics measurement;
l. Atherosclerosis: Deposits of fat, cholesterol, calcium, and clotting materials, known as fibrin in the innermost layer of arteries (endothelium), which results in clogging of the arteries.

In embodiments, catheterization of the left side of the heart is performed by passing the catheter through an artery. In embodiments, catheterization of the right side of the heart is performed by passing the catheter through a vein.

DETAILED DESCRIPTION

Disclosed herein are methods, systems, and devices for coordinating, controlling, and operating medical devices, for example surgical devices. In embodiments, "surgical devices" can comprise any instrument used in surgery, for example, catheters, grasping instruments, retractors, needles, edged devices, imaging devices, combinations thereof, and the like. Disclosed herein are integrated surgical systems that provide increased coordination and control of surgical devices, for example catheters, thus enabling better patient results with reduced risk at lower cost.

Disclosed embodiments comprise a handle assembly comprising a lumen and a shell, housing, or frame, that increases the degree of control and precision of surgical instrument use. Disclosed embodiments can mechanically "fix" or maintain the position of multiple surgical instruments in relation to each other, for example fix the position of a surgical device such as a catheter in relation to another surgical device such as an imaging device, for example along the long axes of both devices. This allows the operator to better-visualize and control the precise location of the surgical devices. Disclosed embodiments can comprise a long axis, for example a long axis comprising means for mechanically and reversibly linking the long axes of multiple surgical devices such as catheters.

In embodiments, the handle assembly can comprise interior "void" regions or locks, snaps, or clips (or combinations thereof) that encompass or partially encompass and reversibly secure medical devices. In embodiments, the handle assembly can comprise a frame to which medical devices can be reversibly secured, for example using void regions, clips, snaps, locks, combinations thereof, or other suitable attachment devices that in embodiments are integrated into the frame. In embodiments the handle assembly comprises multiple pieces that join together to enclose, support, or fix the surgical devices.

Figure 1:
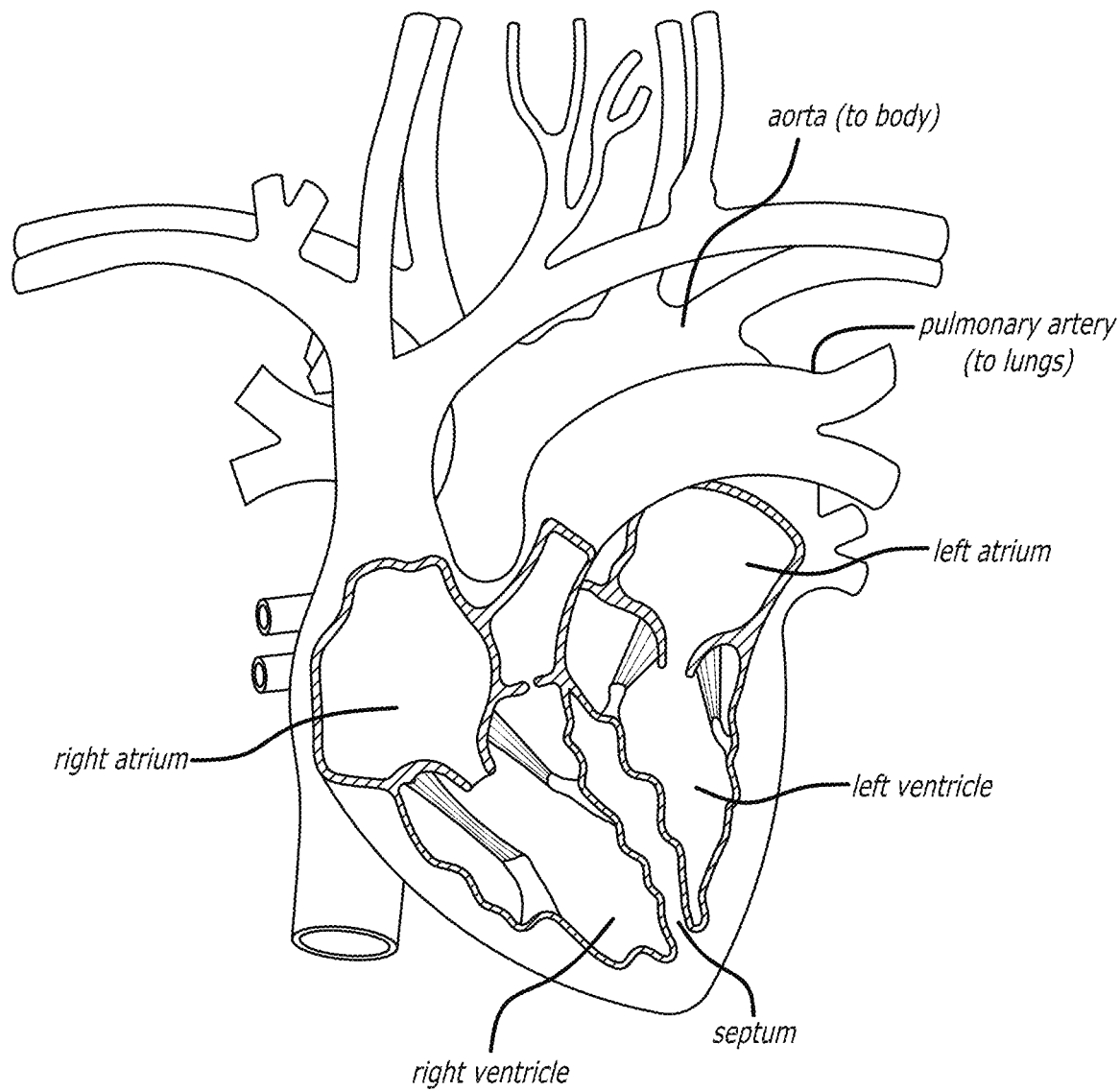
FIG. 1 shows the heart and relevant structures.
Figure 2:
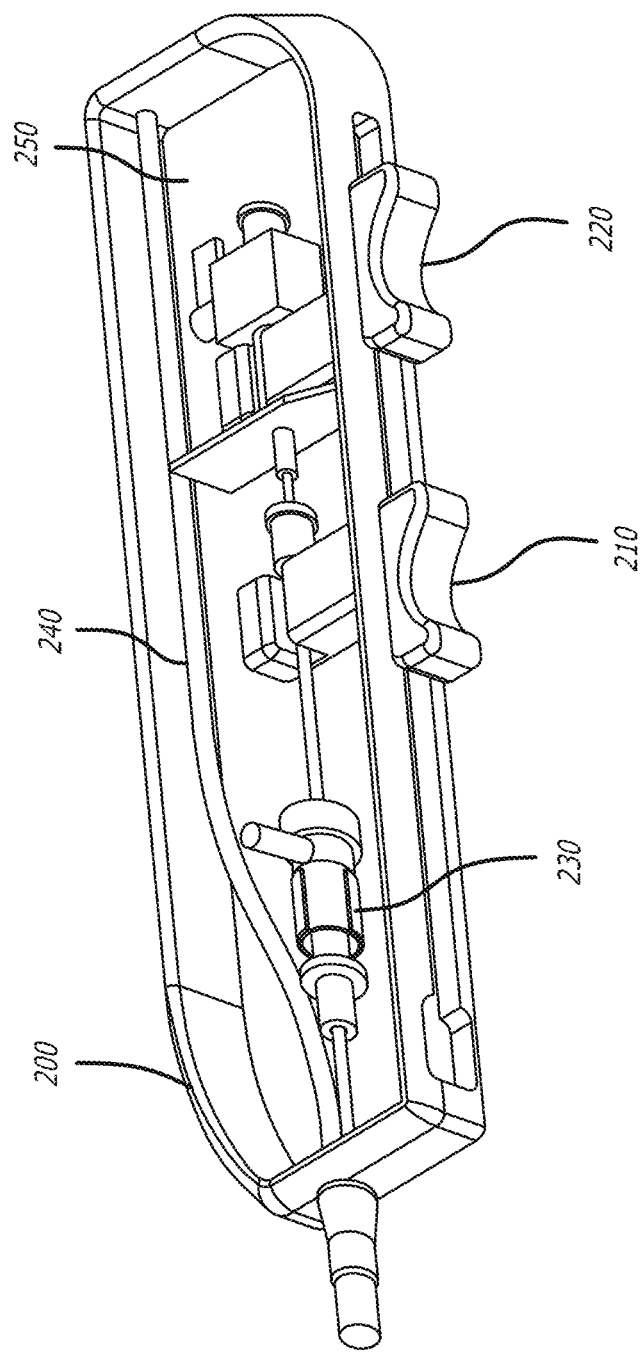
FIG. 2 depicts a handle assembly as described herein.

A disclosed "frame" handle assembly is shown in FIG. 2 (200). Void regions within the assembly extend throughout the inside of the handle assembly, as seen at 250. The void regions are shaped to accommodate the shape of the surgical device(s), or can be of a generic shape that can accommodate various devices, for example catheters. The handle assembly comprises sliders (210, 220) operably connected to the surgical devices for adjusting features of the surgical devices (to connect with lumen 1 [230] or lumen 2 [240]). In embodiments, the sliders comprise "thumb" or "finger" grooves to provide increased control. In embodiments, the position of the sliders can be monitored by their alignment with a colored or striated panel on the handle assembly.

Disclosed embodiments can comprise a surgical device comprising a procedural instrument such as a needle. Disclosed embodiments can comprise a catheter comprising an imaging unit that interacts with the tip of a guide catheter to visualize the tip's location in the vasculature. In embodiments, the imaging unit comprises a generator, a detector, and a transceiver. In embodiments, the transceiver is mounted for axial movement, for example on the guide catheter. In FIG. 2, the lumen of the imaging unit is shown at 240.

Disclosed embodiments comprise systems for performing a procedure on targeted tissue, for example cardiac issue of a patient with an instrument that includes a handle assembly comprising a catheter, for example a catheter formed with a lumen that has a pre-bent or actively bendable section that is located along a distal portion of the catheter. A secondary instrument can be inserted into the lumen of the catheter for advancement therein to extend at least a portion of the secondary instrument beyond the catheter, for example beyond a distal end of the catheter. For example, the secondary instrument can be a needle injector, electrophysiology ablation catheter or a delivery catheter for delivering an embolic protection device or some other device. Also, an imaging unit transceiver can be coupled with the catheter to radiate an energy field in a substantially radial direction from the axis. With this arrangement, the imaging unit is able to simultaneously image a tip on the distal end of the catheter, the secondary instrument such as a needle, and the targeted heart tissue.

Disclosed Systems and Devices
1) Handle Assemblies

Disclosed systems comprise single- or multi-component systems comprising a handle assembly, and at least two surgical devices, for example catheters. In embodiments, one catheter can comprise a localization device, for example an imaging unit, such as an ultrasound unit.

In embodiments, the handle assembly is composed of at least one part. For example, the handle assembly can comprise one or more parts, for example one or more parts that fit together to enclose multiple surgical devices. The one or more parts can reversibly attach to one another through the use of, for example, snaps, clips, locking mechanisms, combinations thereof, or the like. The handle assembly can fully enclose the devices, partially disclose the devices, or a combination thereof.

Disclosed systems comprise multi-component systems comprising a handle assembly that comprises interior void regions, snaps, locks, clips, or other suitable attachment devices that complement the shape of, and thus accommodate, for example, surgical devices such as catheters, for example a guide catheter. These interior void regions, snaps, locks, clips or other suitable attachment devices can reversibly secure the surgical devices to or within the handle, for example along a long axis of the handle assembly.

Disclosed systems can further comprise a handle assembly that comprises interior void regions or clips or other suitable attachment devices that complement the shape of, for example, an imaging unit, for example to coaxially fix the imaging unit. In embodiments, the assembly comprises multiple void regions or clips or other suitable attachment devices such that multiple surgical devices and imaging units can be stably positioned, for example along a long axis of the handle assembly. These multiple void regions or locks or clips or other suitable attachment devices can be oriented, for example, parallel to each other, such that the long axes of the devices positioned within the void regions or to the clips or other suitable attachment devices are, for example, parallel to each other. In embodiments, the long axes of the devices positioned within the void regions or to the clips or other suitable attachment devices are non-parallel to each other.

In embodiments, the handle assembly is composed of one part, such as a frame. For example, the handle assembly can comprise one part that can reversibly attach to surgical devices through the use of, for example, snaps, clips, locking mechanisms, combinations thereof, or the like. In embodiments the handle assembly can partially enclose the devices.

Disclosed systems comprise a multi-component system comprising a handle assembly that comprises a lumen and a frame comprising clips or other suitable attachment devices that complement the shape of, for example, a surgical device such as a catheter. The surgical device can be reversibly secured to the frame via the clips or other suitable attachment devices, for example along a long axis of the handle assembly.

Disclosed systems can further comprise a handle assembly that comprises a frame comprising clips or other suitable attachment devices that complement the shape of, for example, an imaging unit. In embodiments, the assembly comprises a frame such that multiple devices and imaging units can be stably positioned, for example along a long axis of the handle assembly.

In embodiments, the handle assembly comprises ports, for example at the proximal and distal ends, that allow for pass-through of surgical devices or accompanying equipment, for example tubing, etc. In embodiments, associated with these ports are locking devices that can securely attach further equipment, for example tubing or the like.

Further embodiments comprise grooves or slots or ridges on aspects of the assembly contacted by the user to provide for better control of the system.

In embodiments, the handle assembly comprises locking attachment points to secure the imaging unit, catheter, surgical device, etc., to the handle assembly.

In an embodiment, the handle assembly is transparent. In an embodiment, the handle assembly is opaque.

In embodiments, the handle assembly comprises a scale visible to the operator, for example a colored or shaded "ruler" printed or molded on an area of the handle visible to the operator, to aid the operator in measuring distance, for example distance of a needle to or from the tip of a catheter. In embodiments, the handle assembly comprises visual indicators, for example shades or colors, visible to the operator to assist in determining the position of the assembly relative to the treatment area.

Handle assemblies as described herein can be made from any suitable material, for example plastic-based materials, thermoplastic elastomers (TPEs) or thermoplastic olefins (TPOs). In embodiments, the handle assembly is sterilizable, for example the handle assembly is autoclavable. In autoclavable embodiments, the system can be autoclavable in its entirety, or when disassembled into its component parts.

2) Surgical Devices

In disclosed embodiments, the system comprises at least one surgical device, for example a surgical device controlled by the hand of an operator. In embodiments the surgical device comprises an invasive device such as a catheter, for example a guide catheter designed for cardiovascular, urological, gastrointestinal, neurovascular, or ophthalmic applications.

Structurally, the guide catheter defines an axis, and comprises a proximal end and a distal end. It further comprises at least one lumen that extends between the proximal and distal ends of the guide catheter. Further, the lumen is dimensioned to receive, for example, a needle injector that includes a needle for injection into the myocardium, or needle to remove biopsy or a wire that passes through the lumen of the catheter to navigate the vasculature, such as by crossing heart valves or septal defects. In embodiments, an extracorporeal source of a fluid (e.g. biologics: cells, genes, protein and drugs) is attached to the proximal end of the injector for delivery through the needle.

In embodiments, the catheter comprises a distal tip biased to bend into a predetermined configuration (i.e. the guide catheter may have a pre-bent portion), which can position the distal end of the catheter in the vasculature for interception by the energy field produced by the imaging device. Further embodiments comprise a catheter comprising an actuator which can move the imaging unit or the energy field (or both) axially along the length of the catheter to intercept the distal tip of the catheter.

Disclosed embodiments utilize a generator, in combination with a transceiver, to radiate an energy field into the vasculature. This radiation can be in a substantially radial direction from an axis of the guide catheter, for example the long axis of the guide catheter. In embodiments, when the tip is in the energy field, energy (e.g. ultrasound energy) will be reflected from the tip. Also, the energy will be reflected by target tissue, such as the heart. In embodiments, a needle can then be advanced through the lumen of the guide catheter for extension of the needle beyond the tip and from the distal end of the guide catheter for use at a treatment site. In embodiments, a guide wire may be advanced through the catheter. In embodiments, a detector that is electronically connected to the transceiver will then receive and evaluate the signal of reflected energy to determine where exactly the tip is located, relative to target tissue (e.g. heart), in the energy field. A needle injector can then be advanced through the lumen of the guide catheter for extension of a needle beyond the tip and from the distal end of the guide catheter for use at an injection site. In embodiments, a guide wire, rather than the needle injector, can be advanced through the catheter. Disclosed embodiments comprise multiple catheters integrated with multiple imaging devices. For example, disclosed embodiments can comprise multiple imaging means, for example 2D, 3D, 4D, or the like.

Figure 3:
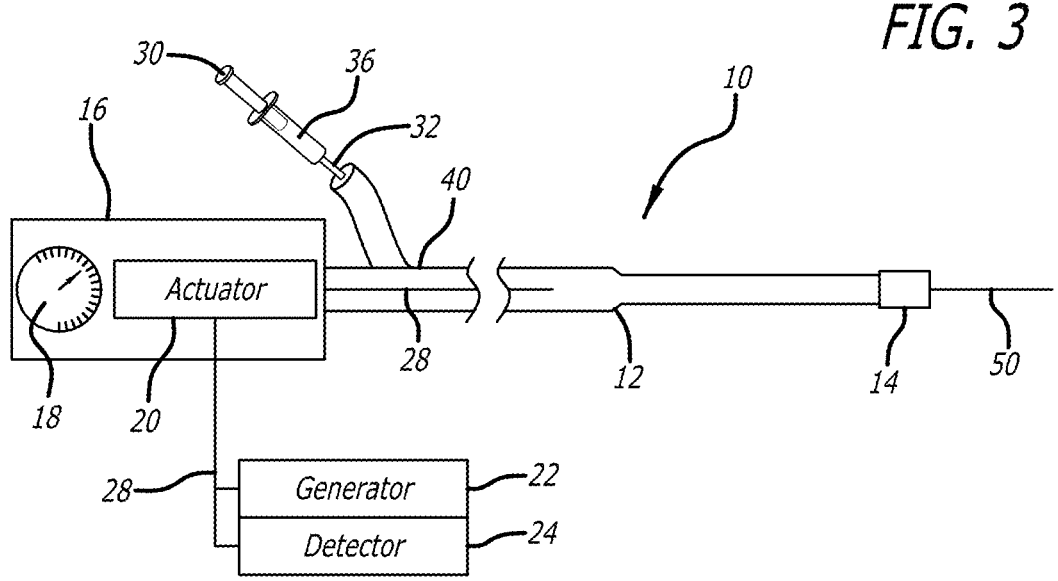
FIG. 3 is a schematic drawing of a catheter for use with a system disclosed herein.

An exemplary catheter suitable for use with disclosed handle assemblies is shown in FIG. 3. As shown, the system 10 includes a guide catheter 12 that has a tip 14 at its distal end. The system 10 also has a handle 16 that is mounted at the proximal end of the guide catheter 12, with an actuator 20 being included as part of the handle 16.

Still referring to FIG. 3, guide catheter 12 can be used with a needle injector 30. More specifically, the needle injector 30 includes a needle wire 32 that has a needle 34 formed at its distal end (see FIG. 4). A fluid source 36 is also provided for the injector 30, and this source 36 can hold a fluid that includes biologics (e.g. cells, genes, protein and drugs) for delivery through the injector 30. As shown, access into the lumen 38 (see FIG. 4) of the guide catheter 12 for both the needle 34 and the needle wire 32 of the injector 30 is provided via a y-site 40.

Figure 4:
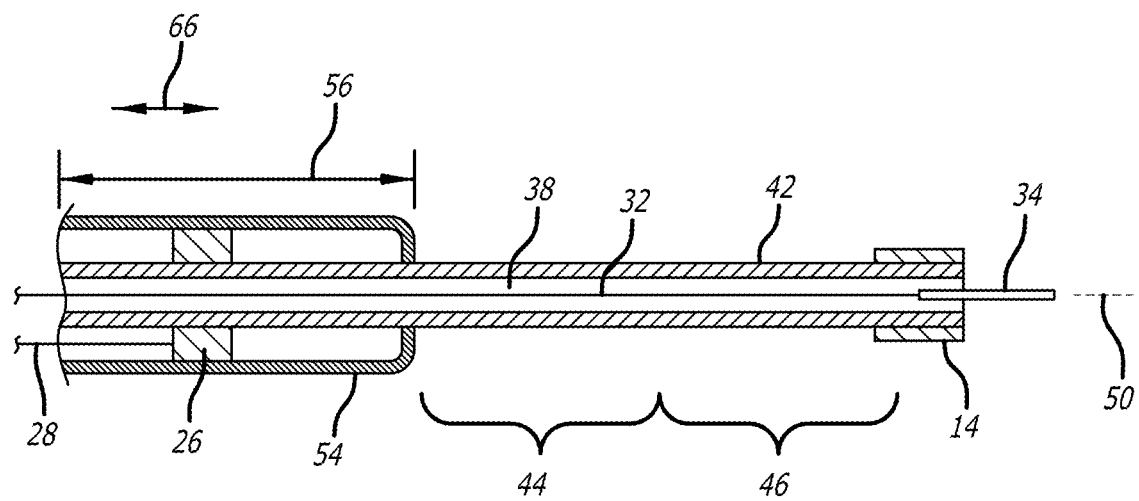
FIG. 4 is a cross-sectional view of the distal portion of a guide catheter as described herein, as seen along line 2-2 in FIG. 3.

In embodiments, the guide catheter 12 can be reconfigured. In FIG. 4 it is shown that a bendable section 42, at the distal portion of the guide catheter 12, can be considered as having at least one reconfigurable part 44. Alternatively, there can be an additional reconfigurable part 46. Various devices have been proposed for bending or steering a catheter through the vasculature of a patient. In disclosed embodiments, any such device would be suitable for reconfiguring the guide catheter 12.

Another structural aspect of the guide catheter 12 that is of more general importance for the entirety of the system 10 concerns the actuator 20 (FIG. 3). More specifically, the manipulation of the imaging unit and the consequent movement of the transceiver 26 is essential for the operation of the system 10.

Disclosed systems comprise a surgical device and localization device such as an imaging unit, wherein the imaging unit provides an energy field that can be used to visualize all or part of the surgical device. For example, in systems comprising a catheter, the energy field can be placed to visualize the tip of the catheter. In embodiments, the energy source can be an ultrasound source. In embodiments, the imaging unit radiates an energy field in a substantially radial direction from the long axis of the unit for the purpose of locating aspects of the assembly, for example a catheter, a catheter tip, a needle, and combinations thereof.

In further embodiments, the imaging unit comprises an actuator that is positioned in the handle of the guide catheter to move the transceiver axially along the guide catheter. In embodiments the actuator comprises an activation wire wherein a first end of the activation wire is attached to the transceiver and a second end is engaged with, for example, a dial. Manipulation of the dial will then produce an axial movement of the transceiver along the guide catheter. Structurally, the operative components of the actuator can be selected as any one of several well-known types, such as a rack and pinion, a lead screw or a reel.

Referring to FIG. 3, the actuator 20 is manipulated during an operation of the system 10. The system 10 includes an energy generator 22 and a detector 24. More specifically, both the energy generator 22 and the detector 24 are electronically connected to a (as seen in FIG. 4) transceiver 26 via an activation wire 28. The activation wire 28 can be manipulated by the actuator to move the transceiver 26 (as seen in FIG. 4). Collectively, the energy generator 22, detector 24 and the transceiver 26 are herein referred to as an imaging unit.

With reference to FIG. 4, the guide catheter is formed with a sleeve 54. Transceiver 26 is moveable inside the sleeve 54 by a manipulation of the actuator. More specifically, movements of the transceiver by the actuator are made on the guide catheter 42, through a range 56, in directions back and forth along the axis 50 indicated by arrows 66. The energy field is radiated from the transceiver 26. In detail, the energy field will be primarily oriented in a direction perpendicular to the axis 50, and will be radiated whenever the transceiver 26 is activated by the generator. Although the generator can generate ultrasound energy, any other type of energy field that is known for use as an imaging modality is suitable (e.g. OCT). Further, although a two-dimensional field of ultrasound energy is typical, a three-dimensional ultrasound field can also be used.

In embodiments comprising a catheter comprising a tip, once there is coincidence (i.e. when the tip of the guide catheter is located and visualized in the energy field), the tip will reflect a signal. Importantly, this signal is useful for further positioning of the distal tip and for advancing the needle from the guide catheter and into the injection site. For an alternate embodiment, the distal portion of the catheter can be steerable, rather than being pre-bent.

Systems described herein are compatible with other imaging systems common to the field, and can be used together with one or more of these other imaging systems to accurately deliver and view the needle or other secondary instrument as it is introduced into the heart or other tissue. These other imaging systems include, but are not limited to, 2D ultrasound, 3D ultrasound, 4D intra-cardiac echo MRI, MRI integrated picture, the NOGA mapping system (Cordis), angiography, Optical Coherence Tomography (OCT), CT, PET/nuclear imaging, a 3D mapping system, 3D left ventricle angiogram and 3D echocardiogram.

Methods of Use

Disclosed herein are methods comprising use of a handle assembly mechanically coupling a surgical device and an imaging device. In embodiments, the surgical device can be a hand-held surgical device, for example a catheter. In embodiments, the imaging device provides an energy field used for visualizing all or part of the surgical device.

Disclosed methods comprise medical procedures such as catheterization, for example using a handle assembly as described herein to hold the catheter and the energy source and thereby fix the relative positions of the catheter and the energy source, such that at least a portion of the catheter is within the energy field.

Disclosed methods comprise catheterization, for example cardiac catheterization. For example, disclosed methods comprise septal puncture, biopsy, heart valve repair or replacement, balloon valvuloplasty, treatment of blood clots, and diagnostic testing. Diagnostic tests suitable for use with disclosed methods comprise coronary angiogram or angiography, intra-cardiac echocardiography, optical coherence tomography (OCT), Disclosed methods comprise procedures and treatments of the atrial septum. For example, disclosed methods comprise puncturing the atrial septum, crossing the atrial septum with a wire (for example, to perform mitrel valve repair or atrial ablation), atrial septal defect (ASD) closure, and patent foramen ovale (PFO) closure or left atrial appendage closure.

Further disclosed embodiments comprise, for example, crossing the aortic valve, delivering cells (for example stem cells) or active agents to the endocardium, crossing the ventricular septum and repairing or replacing a heart valve.

EXAMPLES

The following non-limiting examples are provided for illustrative purposes only in order to facilitate a more complete understanding of representative embodiments. These examples should not be construed to limit any of the embodiments described in the present Specification.

Example 1

Loading of the Handle Assembly

Figure 6:
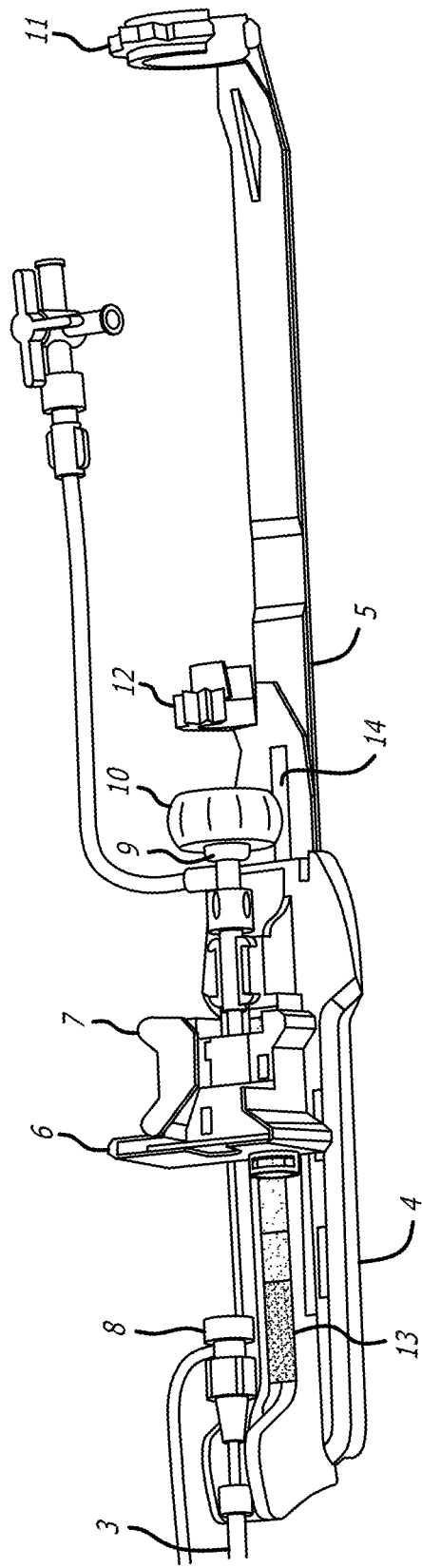
FIG. 6 shows a handle assembly as described herein, including attachment points and locking mechanisms to secure surgical devices, such as a needle and an imaging system.

The handle assembly is removed from the packaging, as seen in FIG. 6. FIG. 6 shows a dual lumen catheter shaft 3, the rear track 5, the needle slide 6, the needle lock lever 7, the hemostasis valve 9, the Touhy knob 10, the proximal lock 11, the distal lock 12, and a depth indicator 13 comprising colored or other visual cues to gauge placement of the device.

The UltraNav catheter is introduced over a J wire that was previously located into the SVC (superior vena cava) and the UltraNav catheter is positioned in the right atrium.

Figure 11:
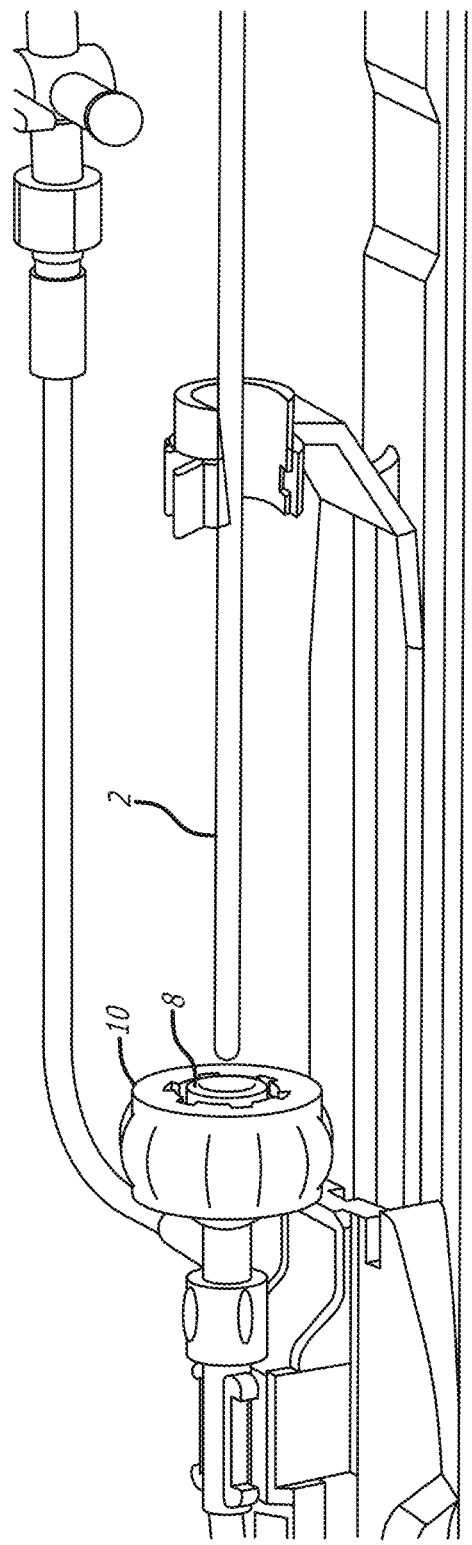
FIG. 11 shows preparation of the handle assembly for use, specifically loading an AcuNav™ catheter into the Touhy Borst valve of the handle assembly.

An ICE (intra-cardiac echocardiography catheter) or AcuNav™ catheter lumen 2 is loaded into hemostasis valve 8 through Touhy knob 10 (FIG. 11).

Figure 12:
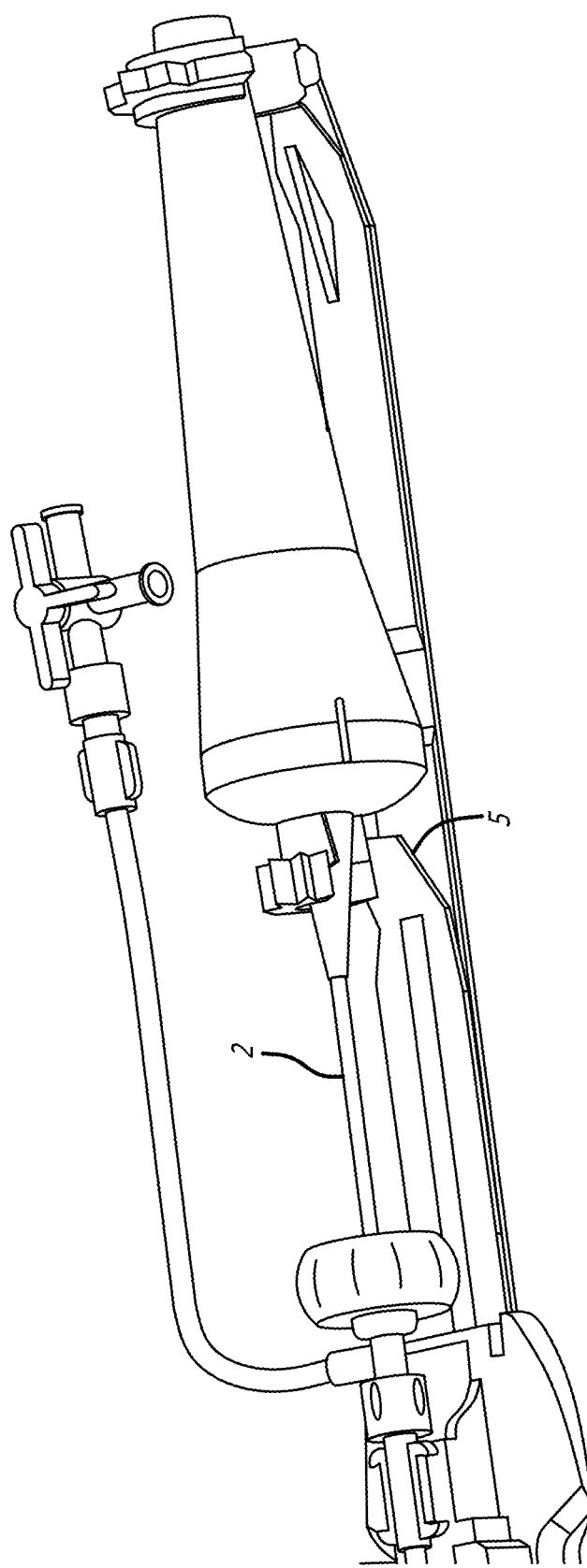
FIG. 12 shows preparation of the handle assembly for use, specifically loading an AcuNav™ imaging catheter into the rear track of the handle assembly.

The ICE (intra-cardiac echocardiography catheter) or 4D ICE, or AcuNav™ catheter 2 is loaded into rear track 5 (FIG. 12).

Figure 13:
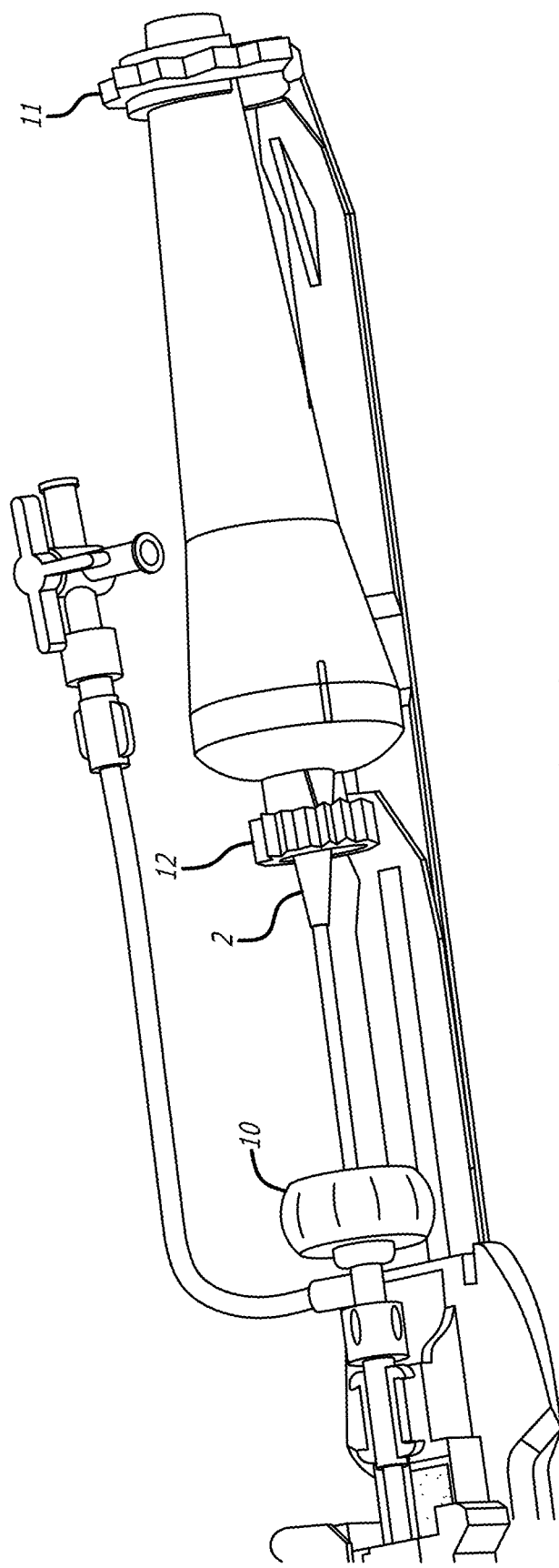
FIG. 13 shows preparation of the handle assembly for use, specifically rotating the distal lock and proximal lock to secure an AcuNav™ catheter into the rear track of the handle assembly.

The distal lock 12 and proximal lock 11 are rotated to secure ICE or an AcuNav™ catheter 2 into rear track (FIG. 13).

Figure 14:
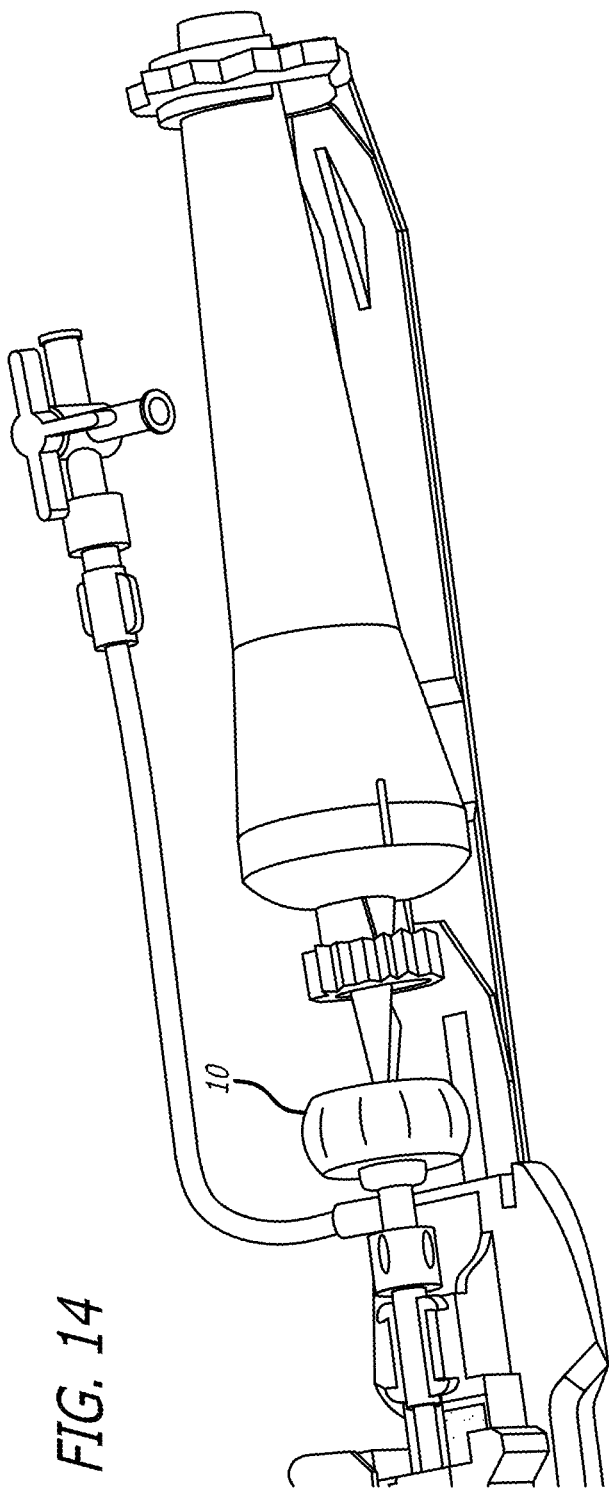
FIG. 14 shows preparation of the handle assembly for use, specifically pushing the rear track and catheter forward while keeping the front body stationary and exposing the catheter tip from the distal lumen of a disclosed handle assembly.
Figure 15:
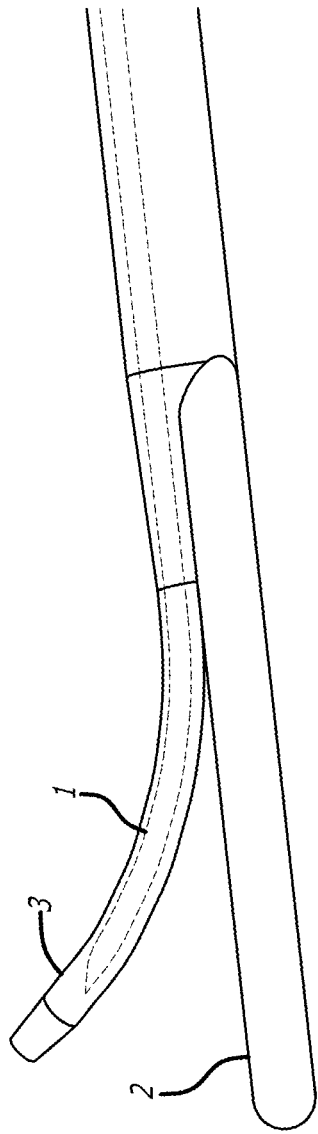
FIG. 15 shows the tip of the catheter. Ultrasound energy is provided at 2.

The rear track 5 and AcuNav™ are pushed forward (FIG. 14), keeping the front body stationary and exposing the AcuNav™ tip 1 from the distal lumen of the handle assembly shaft 3 (FIG. 15).

Figure 16:
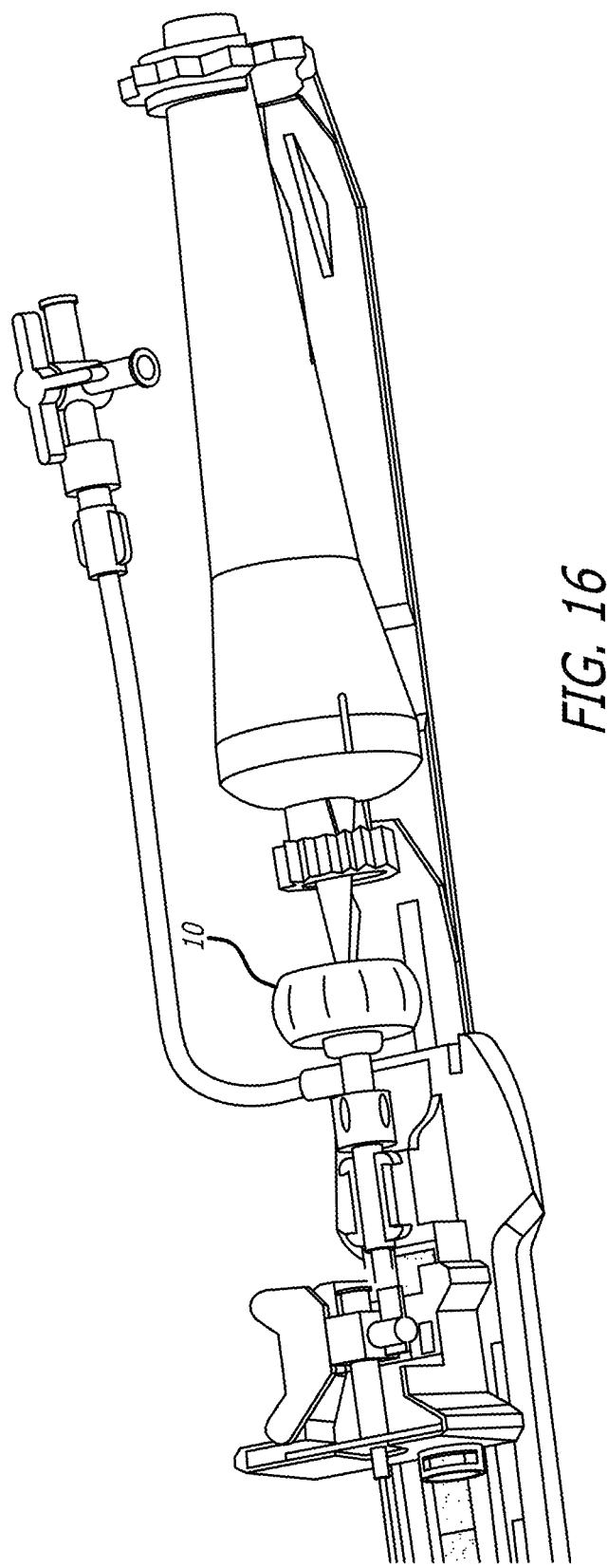
FIG. 16 shows preparation of the handle assembly for use, specifically locking of the catheter position by rotating the knob and closing the Touhy valve onto the catheter shaft. Desired positioning location is achieved by using the depth indicator (shaded area) as a guide. The handle is now loaded.

The AcuNav™ position is locked by rotating the knob, and closing the Touhy valve 10 onto the AcuNav™ shaft (FIG. 16).

Figure 7:
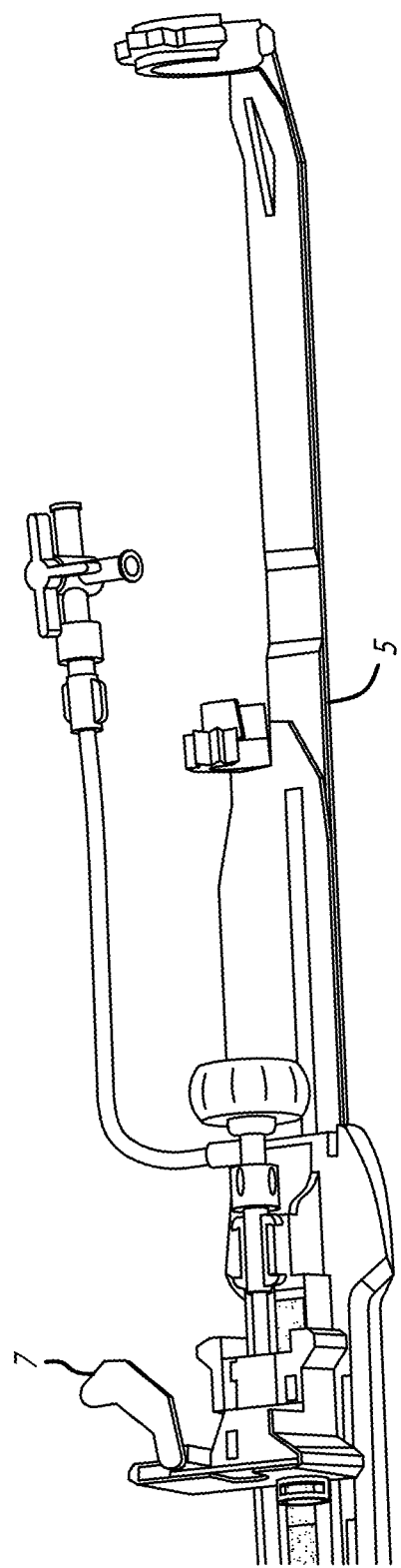
FIG. 7 shows the open needle lock lever and retracted rear track of a disclosed handle assembly. The handle assembly is ready for loading of a surgical device.

The needle lock lever 7 is opened and the rear track 5 retracted (FIG. 7).

Figure 8:
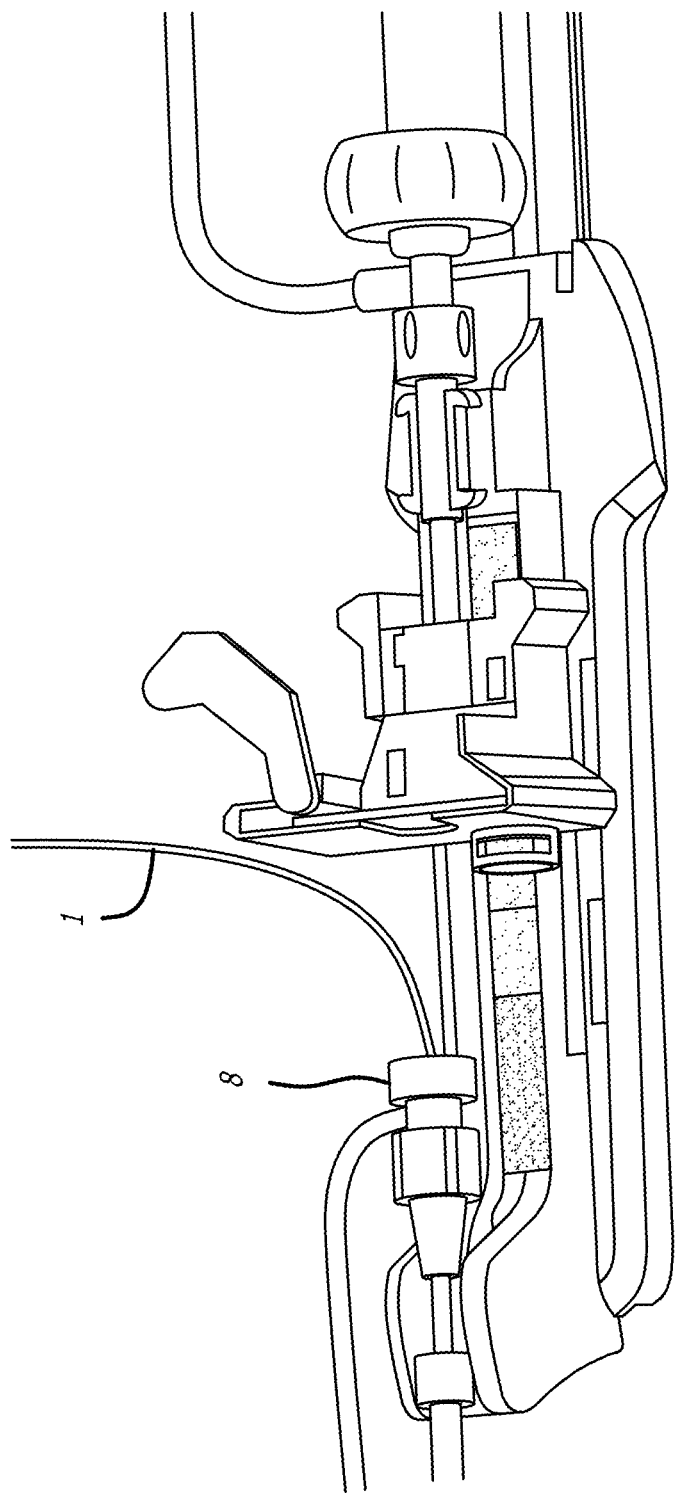
FIG. 8 shows preparation of the handle assembly for use, specifically loading of a needle (for example, Brockenbough or Baylis) into the hemostasis valve, ensuring the needle does not protrude out of the distal end of the catheter tip. The handle provides visual indication of instrument protrusion depth via colored or cross-hatched areas.

A needle 1 is loaded into the hemostasis valve 8, making sure the needle does not protrude out of the distal end of the catheter tip (FIG. 8) by positioning the needle slide within the proximal-most shaded area of the depth indicator.

Figure 9:
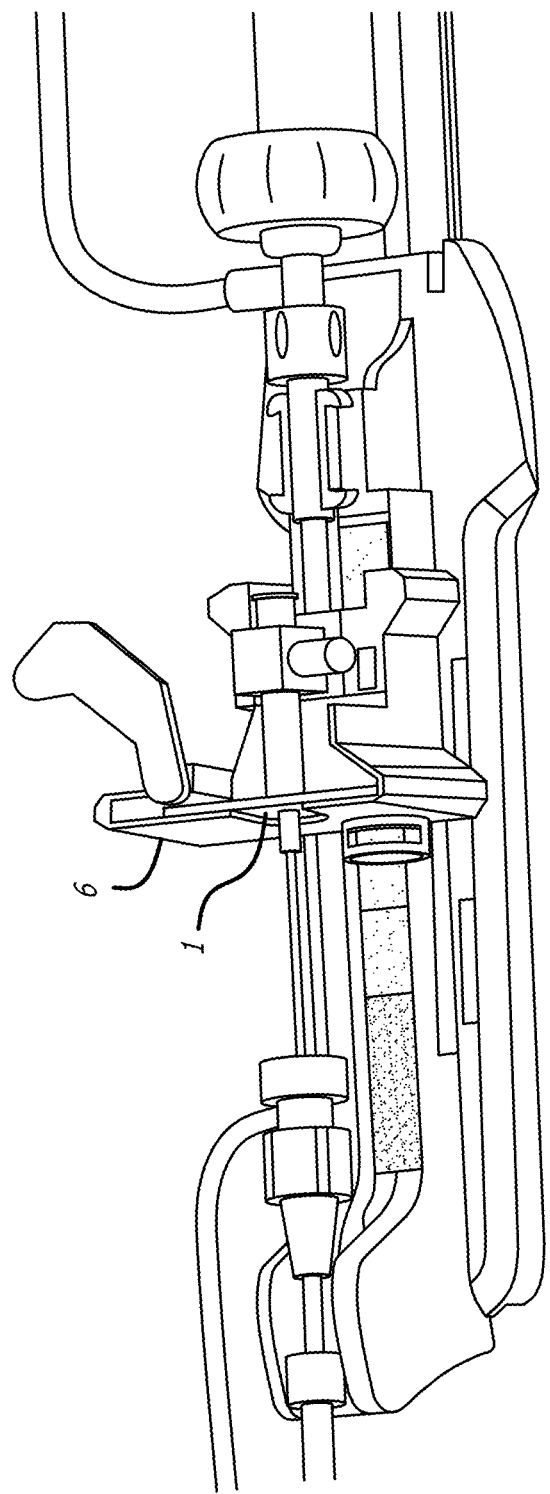
FIG. 9 shows preparation of the handle assembly for use, specifically positioning the needle hub into the needle slide of the handle assembly.

The needle hub 1 is positioned into the needle slide 6 (FIG. 9).

Figure 10:
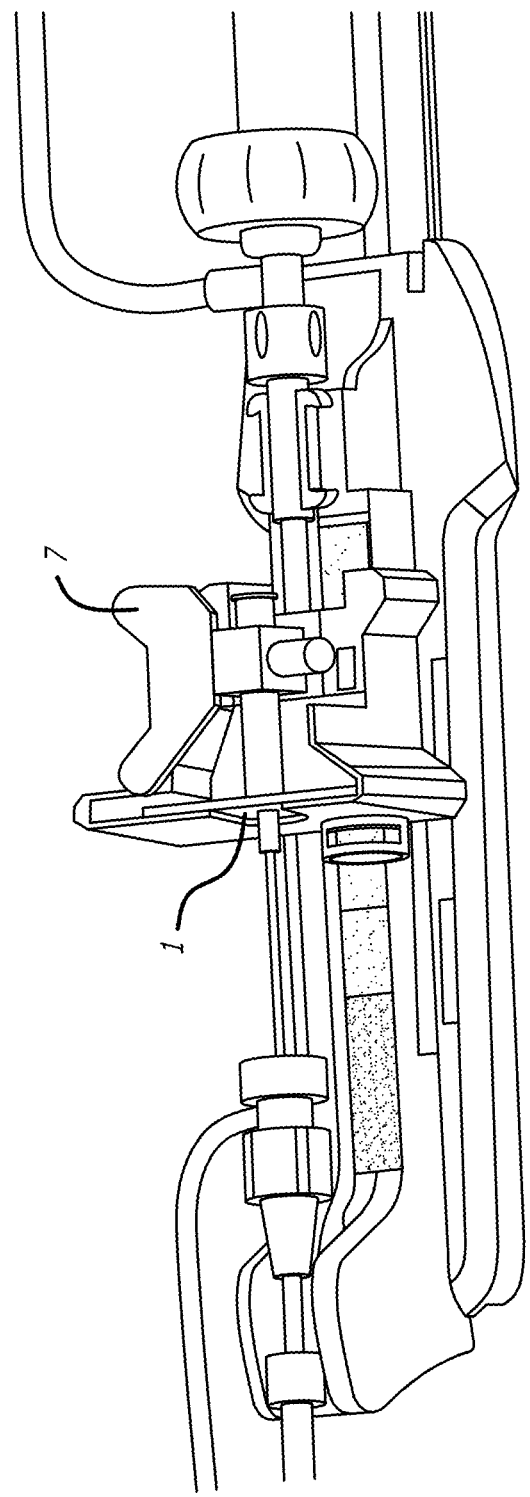
FIG. 10 shows preparation of the handle assembly for use, specifically rotation of the needle lock lever to secure the needle hub into the needle slide of the handle assembly.

The needle lock lever 7 is rotated to secure needle hub 1 into the needle slide (FIG. 10).

Figure 17:
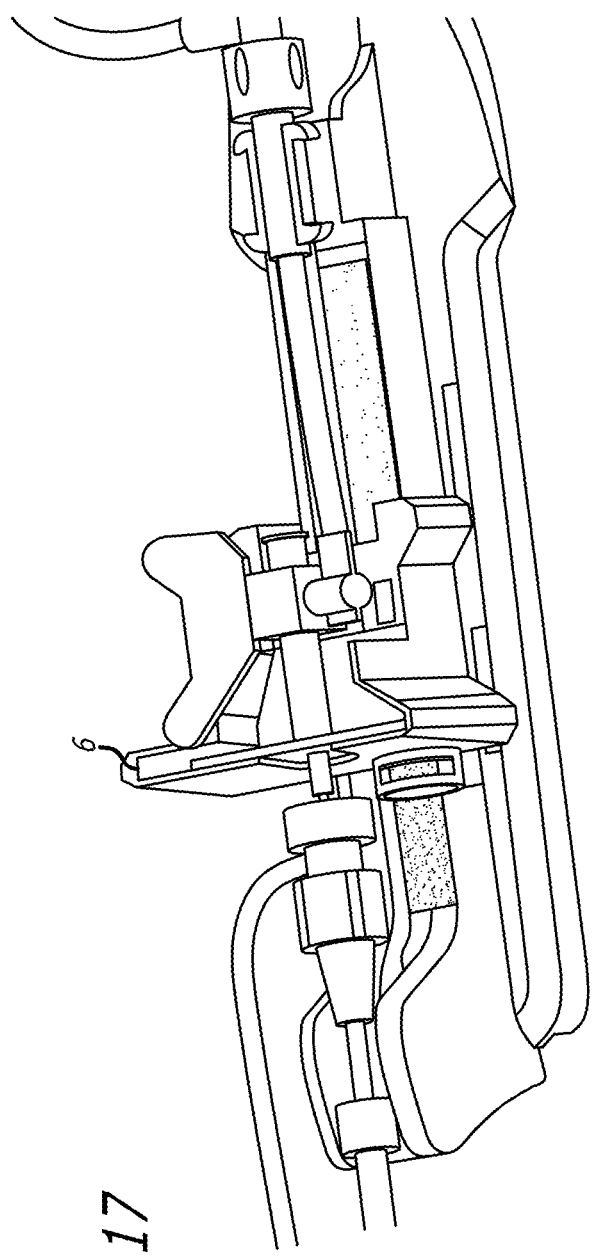
FIG. 17 shows preparation of the handle assembly for use, specifically pushing the needle slide forward to protrude the needle out of the lumen of the handle assembly.
Figure 18:
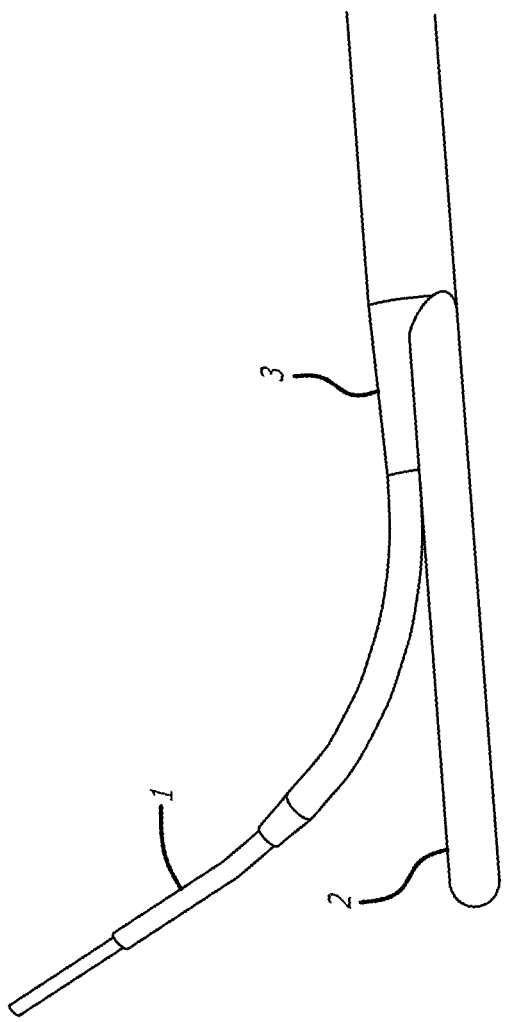
FIG. 18 shows the tip of the catheter.
Figure 19:
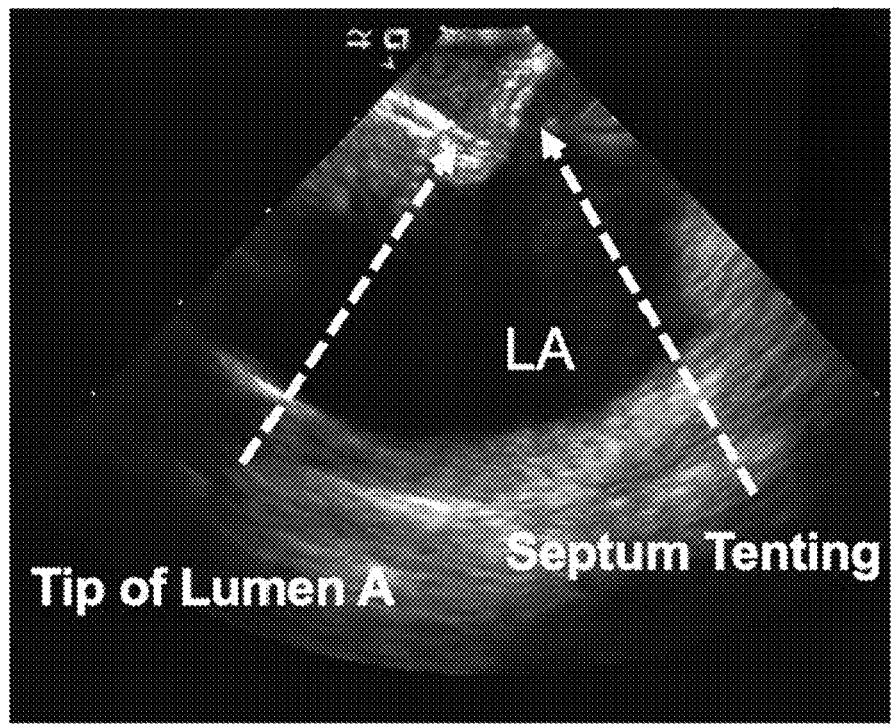
FIG. 19 is an image of a disclosed handle assembly in use. The tip of catheter Lumen A is clearly visible tenting the septum prior to puncture.

The assembly is moved into position for use (FIG. 17). The needle slide is pushed forward to protrude the needle 1 out of the handle assembly catheter shaft 3 (FIG. 18).

The needle is advanced into the most distal section of the shaded depth indicator to properly make a puncture.

Example 2

Real Time Visualization of Cardiac Structure and Simultaneous Diagnosis and or Intervention All current visualization and intervention techniques on the cardiac structure such as septal puncture, catheter ablations, valve repair or replacements, and left appendage closures are performed using imaging equipment that is separate from procedural equipment; this can lead to a frequent loss of visualization during heart and respiratory motion.

The purpose of the disclosed catheter handle assembly is to incorporate and coordinate the ultrasound imaging catheter or catheters (2-D or 3-D and 4-D imaging) in one lumen (Lumen A) and other equipment in a second lumen (Lumen B), such as a needle for septal puncture, ablation catheter, or any catheter to repair the valve and so forth. This allows the direct and simultaneous real-time visualization of such catheters and real-time visualization of the interaction of such catheters with the cardiac tissues, despite continuous cardiac motion. This method and design also allows for transporting catheters between the heart chambers from right to left and vice-versa. The procedure is done by one operator while the patient is awake. The procedure will reduce the need for transesophageal echo (TEE) and anesthesia.

Procedure description: the handle assembly lumen was introduced over J wire 0.035 through the femoral vein and positioned in the SVC (superior vena cava). The ultrasound catheter was introduced into Lumen A, up to the end or tip, before or after introducing the catheter to the SVC. A needle or other catheter was introduced to lumen B up to 1-2 mm proximal to the tip. After introducing needle catheters to the tip, an ultrasound catheter was advanced 1-2 inches to visualize the tip of lumen B. When the tip of lumen B was seen clearly, the handle assembly locked the ultrasound catheter in place. The system can be rotated, pulled back or advanced as one system toward the intended target. Or after ultrasound visualizing the target area of the septum for septal puncture the ICE catheter can be hold in place and the UltraNav catheter pulled back until illuminated by the ultrasound beam.

Scenarios of Procedures:
  a. Septal puncture: After positioning the catheter in the upper Right Atrium (RA) and the tip of Lumen B is seen by ultrasound in Lumen A, the catheter is pulled back with gentle counterclockwise rotation till one can visualize the interatrial septum, and the tip of lumen B is tenting the septum at the intended location. Then the catheter can be manipulated by rotating, pulling back, or advancing to the exact location of the intended site of the fossa or septum. The needle will be advanced through the septum from the right atrium to the left atrium. Bovie can be used as needed and in case of a thick or aneurysmal septum. Once the tip of Lumen B is advanced over the needle into the left atrium by a few millimeters, the needle is removed and the amplatzer super stiff wire 0.035, or other stiff wire is advanced through Lumen B to the pulmonary vein or left atrium. The catheter can be removed after a wire is placed in the pulmonary vein or if another wire such as, a pro track that curves on itself, can be placed in the left atrium. Other catheters can also be advanced from the right atrium to the left atrium over the wire after removing the catheter.
  b. Transport of handle assembly catheter from right to left side: The catheter of the handle assembly with its double lumen can be used to transport other catheters between chambers of the heart. For example, after the catheter crosses from the right atrium to the left atrium, it can be used to transport another ultrasound or ablation catheter from the right to the left atrium.
  c. Ablation of arrhythmia: After septal puncture as described in item (a) and after lumen B crosses the septum, a catheter can be advanced to the left atrium through lumen B. An ultrasound catheter can then be transported through the catheter (Lumen A) to the left atrium where an ablation of the pulmonary vein can be done under direct visualization to verify the location and effectiveness of the ablation. This can enhance the safety and efficacy of the ablation.
  d. Septal closure: After the catheter crosses the septum, a closure device, such as amplatzers, cardioforms, or others can be placed in lumen B and the ultrasound in lumen A. Under direct visualization one can measure the cardiac anatomy and choose the correct device size, while delivering the device safely to verify the outcome all at the same time.
  e. Repairing tricuspid valve: Currently, repairing the tricuspid valve is done with TEE (trans-esophageal echocardiography) or under separate ultrasound guidance. The handle assembly provides one physician the ability to operate the system with consistent image quality while the heart is in motion. This eliminates the need for another doctor or a technician. It also eliminates the need for general anesthesia and reduces the risk to the patient. TEE has limitations with visualizing the tricuspid valve well enough to enable valve repair, therefore, the catheter can provide a clear and accurate intra-cardiac image.
  f. Cannulation coronary sinus: Currently, a device is positioned in the coronary sinus under direct fluoroscopy and visualization of the coronary sinus ostium is possible. The handle disclosed assembly can engage the ostium and deliver a wire to the coronary sinus under direct visualization. It can assist in pacemaker lead placement, in device placement to repair the mitrel valve, such as the Carillon device, and so forth.
  g. Left atrial appendage (LAA) closure: The ability to cross with an ultrasound catheter as noted in item (b), will allow the physician to measure the ostium of the left appendage and place the appropriate device in the appendage under direct visualization, and then obtain immediate feedback on the outcome.
  h. Repairing/replacing Mitral Valve: Similar description to the tricuspid vale noted in item (e).

Example 3

Biopsy

A 60 year old man requires a heart biopsy. A handle assembly as disclosed herein is used to integrate a catheter comprising a tissue sampling device with an imaging unit to visualize the catheter tip during the procedure.

Example 4

Balloon Valvuloplasty

A 60 year old man requires balloon valvuloplasty. A handle assembly as disclosed herein is used to integrate the catheter with an imaging unit to visualize the catheter tip and Balloon location and inflation during the procedure.

Example 5

Vascular Function Testing

A 44 year old woman requires vascular function testing. A handle assembly as disclosed herein is used to integrate the catheter with an imaging unit to visualize the catheter tip during the procedure.

Example 6

Embodiment Testing

The study was performed in Minneapolis on Jan. 28, 2020. A canine model was used.

The handle assembly used in the study was 15.3 Fr, 68 cm length with 25 mm curved tip section (this tip length fit the animal model best). The small lumen was 0.055" and the large lumen was 0.123".

Figure 5:
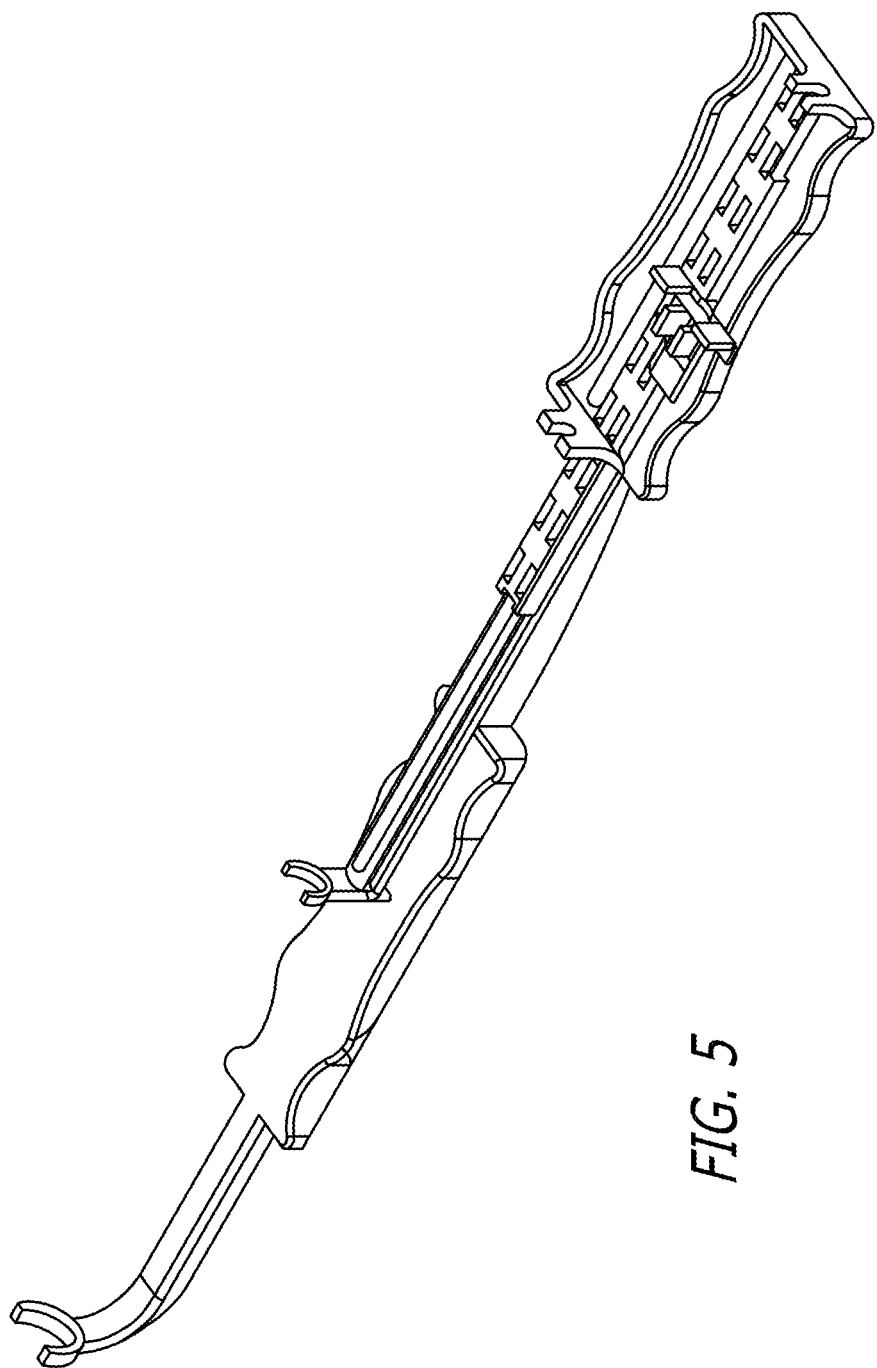
FIG. 5 shows a "frame" handle assembly as described herein. The frame includes "void" regions and clips to accommodate the shape of various instruments.
Figure 20:
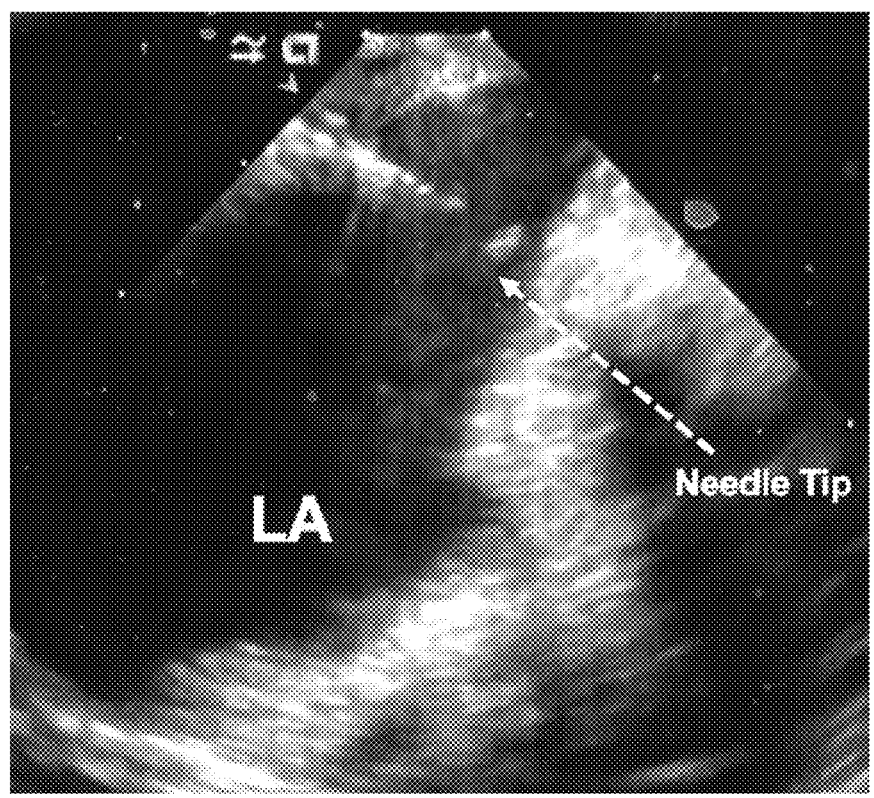
FIG. 20; The needle is clearly visible as having punctured the septum from right atrium to left atrium.
Figure 21:
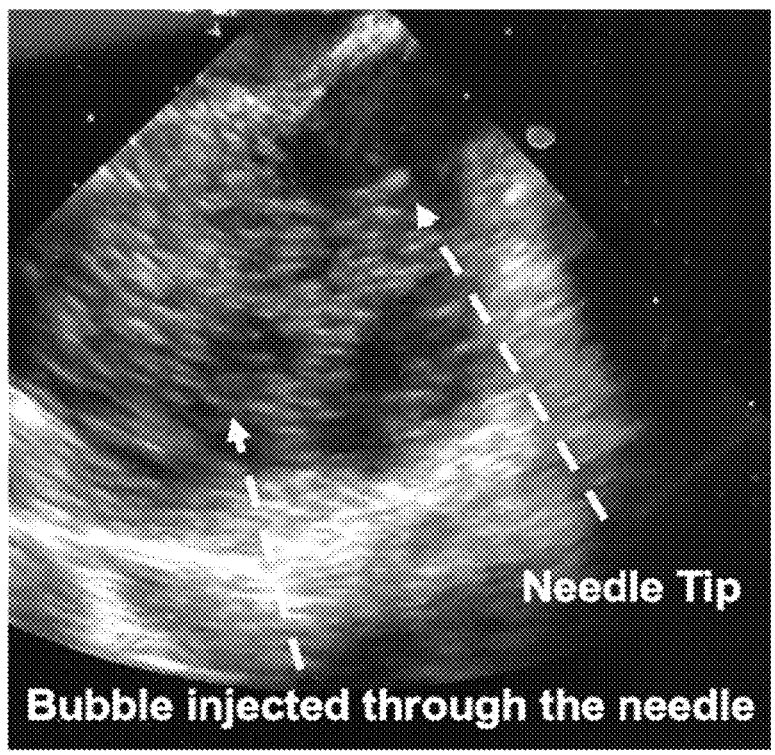
FIG. 21; Bubbles injected through the needle confirm the position of the needle in the left atrium.
Figure 22:
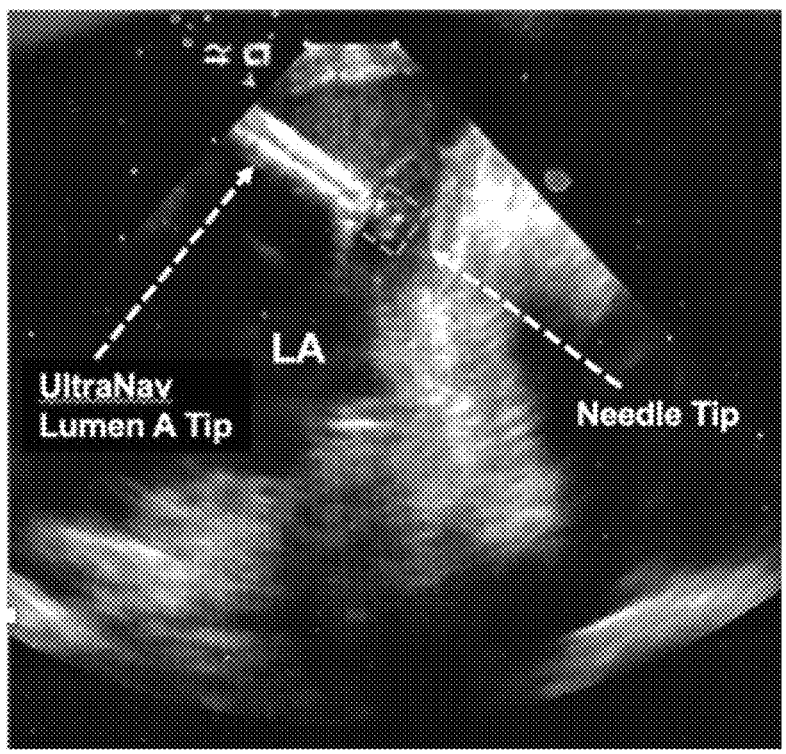
FIG. 22; The catheter tip (lumen A) advanced over the needle into the left atrium.
Figure 23:
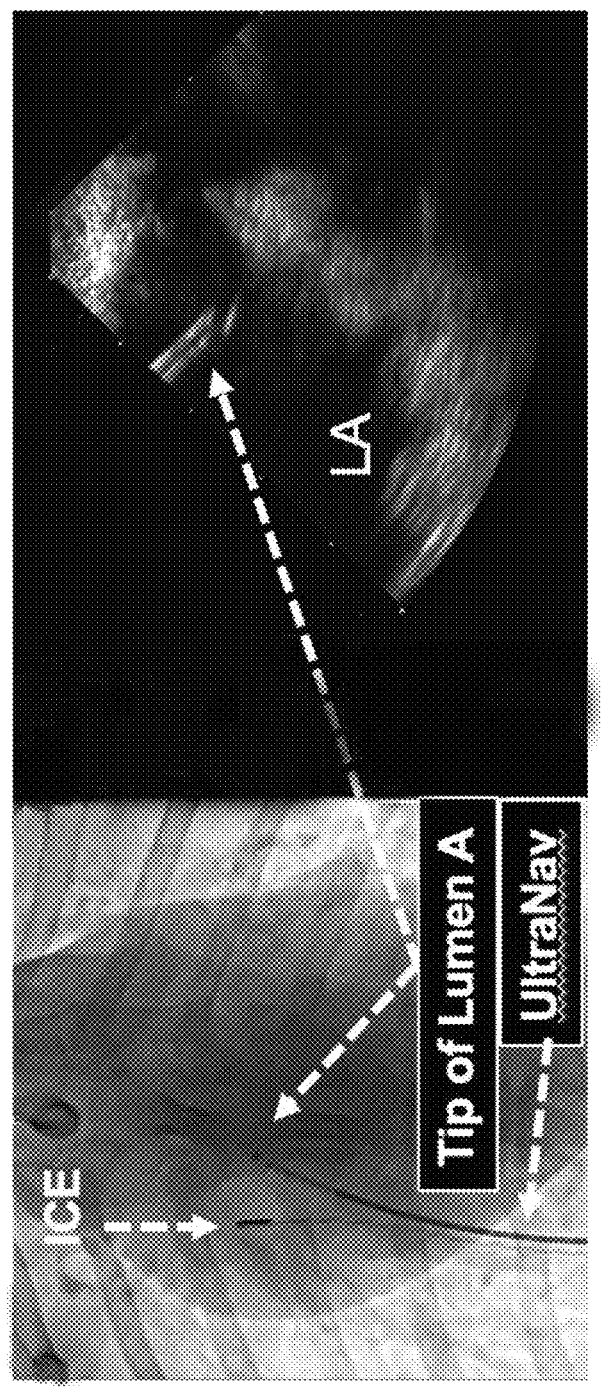
FIG. 23; The tip of the catheter in the left atrium is clearly visible with the ultrasound catheter still in the right atrium.

The handle design is shown in FIG. 5 and FIG. 6. The handle design enabled fixing the relative positions of multiple catheters, so they could be positioned as a unit. The design enables clear visualization of septal punctures (FIG. 20).

Example 7

Animal Study

Non-GLP Prototype Evaluation of the Disclosed Handle Assembly.
Purpose
The study was performed to evaluate a catheter described herein and handle assemblies. Results of the study will be used to further the design and development.
Objectives
The study objectives were to evaluate the handle assemblies and to develop directions for use.

Non-invasive heart procedures are often performed in both the left and right side of the heart. Based on the anatomy of the heart, it is possible to access the left side of the heart from the right side through a trans-septal puncture. This procedure involves a small needle that enters the right atrium of the heart, is poked through the tissue wall that separates the right and left atria, and small tubes are left behind in the left atrium. This procedure allows access to the left side of the heart without accessing an artery and leaving devices in the aorta (largest artery in the body) for extended periods of time. Devices used must be able to both locate the fossa ovalis reliably, and safely puncture the septum in a specific location to provide safe and effective treatment.

The purpose of this study was to test prototypes of the device in a dog heart and prove that the device performs as well as intended.
Protocol
a. One canine was prepared for an acute procedure. Acute evaluations were performed by the physician to show efficacy of the test article in cardiac anatomy. Evaluations were performed until the Sponsor's testing needs were fulfilled. Following acute evaluations, the animal was sacrificed and the target anatomy subjected to gross necropsy evaluations.

| Pre-Procedure Activities | | | | | |
|---|---|---|---|---|---|
| Procedure Type(s) Included: | | | Acute | | |
| Activity | Groups | Time Point Name | Relative Time Pre-Procedure | Freq. | Method |
| Fasting | All | Not applicable | At least hour −12 prior to procedure induction | N/A | Per APS SOP, fast animals. Access to water will not be removed. |
| Procedure prep (acute) | All | Not applicable | After induction | 1× | Per APS SOP, prep animal for surgery, this includes recording the general condition of the animal and vital signs. |

| 5.7.1.2 Pre-Procedure Substance Administration | | | |
|---|---|---|---|
| Procedure Type(s) Included: | | Acute | |
| Substance, Dose, Route, Freq. | Drug Type, Reason | Groups | Relative Time Pre-procedure |
| Midazolam, 0.1-0.2 mg/kg, IM, 1× | Dissociative anesthetic/Benzodiazepine, Induction | All | At induction |
| Butorphanol, 0.05-0.1 mg/kg, IM, 1× | Opioid Analgesic, Analgesia | Al | At induction |
| Propofol, Typical dose 2-8 mg/kg, IV, To effect, PRN | Alkylphenol, Supplemental induction | Al | At induction to maintain surgical plane of anesthesia per APS SOP |
| Isoflurane in 100% $O_2$, 0-5%, Inhal, To effect | Gas anesthetic, Supplemental induction | All | At induction to maintain surgical plane of anesthesia per APS SOP |
| Isotonic Fluid ~5.0-10.0 mL/kg/hour IV CRI | IV fluid-crystalloid, fluid maintenance | All | As needed for prolonged prep time (>30 minutes), as directed by veterinarian or interventionalist/surgeon. |

5.7.1.3 Intra-Procedure Activities

Procedure Type(s) Included: Acute

| Activity | Groups | Relative Time Pre-Procedure | Freq. | Method |
|---|---|---|---|---|
| Vitals Monitoring | All | During procedure | Target every 15 min., not to exceed 30 min. | Per APS SOP, oxygen saturation and heart rate may be recorded. Additional physiological data may also be recorded. |
| Blood gas/electrolyte monitoring | All | During procedure | PRN | Per APS SOP, Arterial or venous blood gas and electrolytes may be recorded at the discretion of the operating room staff to monitor animal health. |
| Anticoagulation | All | Start: After first heparin dose Stops: After acute evaluations have been completed | Target every 30 min., not to exceed 45 min. (Not applicable between baseline and 1$^{st}$ heparin dose) | Measure baseline activated clotting time (ACT). Administer heparin to elevate the ACT above 250 seconds. Additional heparin will be administered as necessary to then maintain the ACT above 250 seconds, and/or in the event that the ACT drops below 250 seconds. |

5.7.1.4 Intra-Procedure Substance Administration

Procedure Type(s) Included: Acute

| Substance, Dose, Route, Freq. | Drug Type, Reason | Groups | Relative Time Pre-procedure |
|---|---|---|---|
| Isoflurane in 100% O$_2$, 0-5%, Inhal, To effect | Gas anesthetic, Maintenance anesthesia | All | During procedure to maintain surgical plane of anesthesia per APS SOP |
| Heparin, Typical dose 20-300 IU/kg, IV, To effect | Coag Factor Xa Inhibitor, Anticoagulation | All | During procedure to maintain appropriate ACT |
| Nitroglycerin, Typical dose, 100-400 mcg, IA, To effect, PRN | Smooth Muscle Relaxant, Vasodilation | All | During procedure to prevent vascular spasm as directed by interventionalist/surgeon |
| Propofol, Typical dose, 2-8 mg/kg, IV, To effect, PRN | Alkylphenol, Supplemental anesthetic | All | During procedure to maintain surgical plane of anesthesia per APS SOP |
| Iso Vue Contrast or Equivalent, As needed, IV or IA | Nonionic Contrast, Vessel Imaging | All | During procedure to obtain adequate image |
| Isotonic Fluid ~5.0-10.0 mL/kg/hour IV CRI; additional volume as needed | IV fluid-crystalloid, fluid maintenance | All | During procedure for maintenance fluid replacement. More volume may be administered to combat hypotension and for volume replacement associated with blood loss. |
| Lidocaine Bolus, 1-2 mg/kg, IV, PRN Lidocaine Drip, typical target of 1 mg/kg/hr, IV, CRI | Antiarrhythmic | All | As needed during procedure to treat arrhythmia as directed by surgeon/interventionalist or veterinarian; DO NOT administer within 15 minutes of amiodarone |
| Amiodarone 50 mg/mL Bolus, 150 mg, over a 10 minute period Amiodarone 0.5 mg/mL Drip, 100-200 mL/hr, IV, CRI | Potassium channel blocking agent, antiarrhythmic | All | As needed during procedure to treat arrhythmia as directed by surgeon/interventionalist or veterinarian; DO NOT administer within 15 minutes of lidocaine |
| Calcium Chloride, PRN to effect with typical dosages between 250-1000 mg, IV | Strengthens myocardial contraction | All | During procedure as needed when a decrease in contractility is observed during procedure. |
| Phenylephrine Bolus, 0.1 mg/mL, PRN (typically 1-3 mL), IV Phenylephrine Drip, 40 ug/mL, PRN (typically 5-20 mL/hr), IV | Hypotension | All | As needed to treat hypotension if blood pressure mean drops below ~50 mmHg as directed by surgeon/interventionalist or veterinarian |
| Hetastarch, IV PRN, in approximate equal volume of blood loss at 10-20 ml/kg over 30 minutes, then 1-2 ml/kg/hr not to exceed 20 ml/kg/day. | Hypovolemic | All | During procedure to replace blood loss |
| Heparin, Typical dose 20,000 IU, IV, 1× | Coag Factor Xa Inhibitor, Anticoagulation | All | Prior to euthanasia |
| Euthanasia Solution, Per controlled doc. R-S-IL-GN-OP-009-01, IV, to effect | Barbiturate, Humane Euthanasia | All | End of Procedure |

| 5.7.1.5 Intra-Procedure Methods | | | | |
|---|---|---|---|---|
| Procedure Type(s) Included: | | Acute | | |
| | | | Method | |
| Activity | Group | Femoral Vein | Femoral Artery | Jugular Vein |
| Access | All | Primary vascular access will be bilateral femoral vein access. Sheaths will be ≤20 Fr size. Femoral artery access will be obtained for pressure monitoring and ACT monitoring. The jugular vein(s) may also be accessed in order to complete testing needs. | | |
| Acute Procedure | All | 1. The UltraNav will be prepped for delivery and advanced under fluoroscopic guidance over a suitable off-the-shelf 0.035" guidewire to the level of the superior vena cava.<br>2. The ACUNAV ultrasound catheter (Biosense Webster) will be inserted into the second lumen of the UltraNav.<br>3. The wire will be removed and the needle will be inserted into the catheter and advanced under fluoroscopic guidance until the needle tip is just inside the catheter tip, taking care to not exit the catheter.<br>4. The needle tip will be positioned 1 mm inside the catheter while in the SVC.<br>5. After pulling the catheter from the SVC, advance an ICE catheter to align with catheter tip.<br>6. The UltraNav with ACUNAV and needle will be rotated to visualize the septum in short axis and Bicaval views and to position the needle to puncture the septum in different locations (e.g., fossa ovalis, posterior and inferior, posterior and superior, and anterior part of the septum). Usually the needle curve will be aligned with catheter rotation toward the 5 o'clock position.<br>7. The catheter and needle will be advanced as a unit to tent the septum-fossa. The needle will then be advance slightly to puncture the septum under intracardiac ultrasound guidance with the ACUNAV catheter. Bovie can be used to facilitate the puncture if needed.<br>8. After the puncture is done, the UltraNav catheter will be advanced a few millimeters over the needle<br>9. The needle will be removed and then an Amplatz Super Stiff (Boston Scientific) or Rosen Wire (Cook Medical) will be introduced to the pulmonary or ProTrak Pigtail Wire (Baylis) to the left atrium (LA).<br>10. The ACUNAV catheter will be pulled back to inside its lumen. Then the UltraNav catheter with the ACUNAV will be advanced to the LA, the wire be removed and visualization of the wall of the LA, MV, LAA, and PV will be documented.<br>11. All devices will be removed when the test is complete.<br>12. Steps 1-10 will be repeated using the UltraNav handle accessory.<br>13. The procedure may be repeated multiple times in the animal. | | |
| Euthanasia | All | Per APS SOP, perform euthanasia via lethal injection of euthanasia solution. Verify death by auscultation or pulse monitoring. | | |

Prototypes, 0.035 guidewires and septal crossing needles were provided to testing personnel. The testing facility (APS) provided 16 Fr and 20 Fr introducer sheaths. Two handle prototypes and eight catheter prototypes (listed in the following table) were provided.

| QTY | Tip Length | Fr Size | Length | Small Lumen ID | Large Lumen ID |
|---|---|---|---|---|---|
| 4 | 25 | 15.3 | 68 cm | 0.055 | 0.123 |
| 2 | 30 | 15.3 | 68 cm | 0.055 | 0.123 |
| 2 | 35 | 15.3 | 68 cm | 0.055 | 0.123 |

Results

Digital records of the ultrasound images, x-ray (cine) images and quad views were provided by the test facility. Results are summarized below.

Septal Crossing Attempts

Regular J-tip wire (0.035, 260 cm length, J-tip shape) and 16 Fr introducer sheaths were used in all attempts. The ICE catheter was inserted to lumen B and aligned with the Tip of the catheter. The catheter advanced easily over the J-Tip 0.035 wire. The wire was removed, and the ICE advanced to visualize the septum in short axis and bi-caval views. The needle was then advanced to the tip of lumen A. The catheter was pulled back while keeping ICE in place until the ICE visualized the tip of lumen A, tenting the septum. The needle was advanced to the septum and Bovie (RF) was applied. The needle was seen crossing the septum to the left atrium and verification was made by bubble study and angiography.

Handle used—demonstrated that with the handle assembly the catheters can rotate together as a system without losing the ultrasound. With the system locked together the ultrasound is fixed with respect to the catheter.

Directions for device use suggested by the study experience are as follows.

a. Load an UltraNav™ catheter into the handle.
  b. Load the ultrasound (US) catheter into lumen B of the UltraNav™ catheter.
  c. Align the US catheter beam with the tip of lumen A of the UltraNav™ catheter, pull back the ultrasound catheter to inside the UltraNav™ and lock position.
  d. Insert the guidewire into lumen A of the UltraNav™ catheter.
  e. Introduce UltraNav™ system into the body through 16 F sheath.
  f. Advance the guidewire to the Superior Vena Cava (SVC).
  g. Advance the UltraNav™ catheter over the wire to the SVC h. Advance the US catheter to the desired position with view of the septum and lock the US catheter.
i. Remove the guidewire from lumen A of the UltraNav™ catheter.
j. Load the desired transseptal puncture needle into lumen A of the UltraNav™ catheter.
k. Using the handle, advance the stylet and needle to the start of the blue section indicated on the handle. Then remove stylet.
l. With the US catheter into the desired place, pull the UltraNav™ catheter into the desired position and lock into place the US catheter.
m. Tent the septum.
n. Advance the needle into the red section of the handle and puncture the septum. Bovie can be used to facilitate puncturing the septum.
o. Advance Tip of the catheter over the needle to Left atrium after needle crossed the septum; remove needle.

CONTEMPLATED EMBODIMENTS

Embodiment 1

A method for performing trans-septal heart catheterization comprising use of a system for fixing the relative position of a catheter and at least one surgical device, said system comprising a handle assembly comprising a void region complimentary to the shape of the catheter.

Embodiment 2

The method of embodiment 1, wherein said catheter comprises a dual lumen catheter.

Embodiment 3

The method of embodiment 1, wherein said at least one surgical device comprises an imaging unit.

Embodiment 4

The method of embodiment 3, wherein said imaging unit comprises an ultrasound unit.

Embodiment 5

The method of embodiment 4, wherein said ultrasound unit comprises a 2D, 3D, or 4D ultrasound unit.

Embodiment 6

The method of embodiment 5, wherein said 2D, 3D, or 4D ultrasound unit comprises a 3D ultrasound unit.

Embodiment 7

The method of embodiment 1, further comprising a lock to secure at least one of the surgical devices.

Embodiment 8

The method of embodiment 1, wherein said trans-septal heart catheterization comprises catheter ablation.

Embodiment 9

The method of embodiment 1, wherein said trans-septal heart catheterization comprises valve repair.

Embodiment 10

The method of embodiment 1, wherein said trans-septal heart catheterization comprises valve replacement.

Embodiment 11

The method of embodiment 1, wherein said trans-septal heart catheterization comprises left appendage closure.

Embodiment 12

The method of embodiment 1, wherein said trans-septal heart catheterization comprises valvuloplasty.

Embodiment 13

The method of embodiment 1, wherein said trans-septal heart catheterization comprises balloon valvuloplasty.

Embodiment 14

A system for performing trans-septal heart catheterization comprising use of a system for fixing the relative position of a catheter and at least one surgical device, said system comprising a handle assembly comprising a void region complimentary to the shape of the catheter.

Embodiment 15

The system of embodiment 14, wherein said catheter comprises a dual lumen catheter.

Embodiment 16

The system of embodiment 14, wherein said trans-septal heart catheterization comprises catheter ablation.

Embodiment 17

The system of embodiment 14, wherein said trans-septal heart catheterization comprises valve repair.

Embodiment 18

The system of embodiment 14, wherein said trans-septal heart catheterization comprises valve replacement.

Embodiment 19

The system of embodiment 14, wherein said trans-septal heart catheterization comprises left appendage closure.

Embodiment 20

The system of embodiment 14, wherein said trans-septal heart catheterization comprises valvuloplasty.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, including the best mode known to the inventor for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A method for performing trans-septal heart catheterization comprising use of a system for fixing the relative position of a catheter and at least one surgical device, said system comprising a handle assembly comprising a void region complimentary to the shape of the catheter, and said handle assembly further comprising a retractable rear track.

2. The method of claim 1, wherein said catheter comprises a dual lumen catheter.

3. The method of claim 1, wherein said at least one surgical device comprises an imaging unit.

4. The method of claim 3, wherein said imaging unit comprises an ultrasound unit.

5. The method of claim 4, wherein said ultrasound unit comprises a 2D, 3D, or 4D ultrasound unit.

6. The method of claim 5, wherein said 2D, 3D, or 4D ultrasound unit comprises a 3D ultrasound unit.

7. The method of claim 1, further comprising a lock to secure at least one of the surgical devices.

8. The method of claim 1, wherein said trans-septal heart catheterization comprises catheter ablation.

9. The method of claim 1, wherein said trans-septal heart catheterization comprises valve repair.

10. The method of claim 1, wherein said trans-septal heart catheterization comprises valve replacement.

11. The method of claim 1, wherein said trans-septal heart catheterization comprises left appendage closure.

12. The method of claim 1, wherein said trans-septal heart catheterization comprises valvuloplasty.

13. The method of claim 1, wherein said trans-septal heart catheterization comprises balloon valvuloplasty.

14. A system for performing trans-septal heart catheterization comprising use of a system for fixing the relative position of a catheter and at least one surgical device, said system comprising a handle assembly comprising a void region complimentary to the shape of the catheter, and said handle assembly further comprising a retractable rear track.

15. The system of claim 14, wherein said catheter comprises a dual lumen catheter.

16. The system of claim 14, wherein said trans-septal heart catheterization comprises catheter ablation.

17. The system of claim 14, wherein said trans-septal heart catheterization comprises valve repair.

18. The system of claim 14, wherein said trans-septal heart catheterization comprises valve replacement.

19. The system of claim 14, wherein said trans-septal heart catheterization comprises left appendage closure.

20. The system of claim 14, wherein said trans-septal heart catheterization comprises valvuloplasty.

* * * * *